(12) United States Patent
Wang

(10) Patent No.: US 6,682,647 B1
(45) Date of Patent: Jan. 27, 2004

(54) BISMUTH-BASED ELECTROCHEMICAL STRIPPING ANALYSIS

(75) Inventor: Joseph Wang, Las Cruces, NM (US)

(73) Assignee: New Mexico State University Technology Transfer Corporation, Las Cruces, NM (US)

(*) Notice: Subject to any disclaimer, the term of this patent is extended or adjusted under 35 U.S.C. 154(b) by 272 days.

(21) Appl. No.: 09/854,291

(22) Filed: May 10, 2001

Related U.S. Application Data
(60) Provisional application No. 60/203,536, filed on May 10, 2000.

(51) Int. Cl.[7] .................. G01N 27/26; G01N 27/48
(52) U.S. Cl. .................. 205/775; 204/292; 204/434; 205/789; 205/789.5
(58) Field of Search ................ 205/775, 789, 205/789.5; 204/434, 292

(56) References Cited

U.S. PATENT DOCUMENTS

| | | |
|---|---|---|
| 2,773,020 A | * 12/1956 | Offutt et al. |
| 3,721,618 A | 3/1973 | Reding |
| 3,855,099 A | 12/1974 | Matson |
| 4,052,286 A | 10/1977 | Gray et al. |
| 4,061,917 A | 12/1977 | Goranson et al. |
| 4,834,851 A | 5/1989 | Nidola et al. |
| 5,292,423 A | 3/1994 | Wang |
| 5,391,270 A | 2/1995 | Gui |
| 5,460,710 A | 10/1995 | Williams et al. |
| 5,514,601 A | 5/1996 | Reilly |
| 5,635,054 A | 6/1997 | Girault et al. |
| 5,676,820 A | 10/1997 | Wang et al. |
| 5,804,823 A | 9/1998 | Ramer et al. |
| 5,830,343 A | 11/1998 | Hintsche et al. |
| 5,977,782 A | 11/1999 | Kordecki |

FOREIGN PATENT DOCUMENTS

| | | |
|---|---|---|
| JP | 51112390 A2 | 3/1975 |
| JP | 8136497 A2 | 11/1994 |
| JP | 411045616 A | 2/1999 |

OTHER PUBLICATIONS

Hocevar, S.B., et al., "Bismuth Film Electrode for Advanced Stripping Analysis," *Abstract 1042:* published as part of the *Abstracts: 2001 Pittsburgh Conference on Analytical Chemistry and Applied Spectroscopy*, (Pittcon 2001), New Orleans LA US Mar. 4–9, 2001) actually published approx Jan. 2001.

Achterberg, E.P., et al., "Stripping Voltammetry for the Determination of Trace Metal Speciation and *In–Situ* Measurements of Trace Metal Distributions in Marine Waters," *Analytica Chimica Acta 400*, pp 381–396 (1999), month unavailable.

Florence. T.M., "Anodic Stripping Voltammetry with a Glassy Carbon Electrode Mercury–Plated *in Situ,*" *Electroanalytical Chemistry and Interfacial Electrochemistry*, Vol 27, pp 273–281 (1970), Month unavailable.

Fogg, A.G., et al., "Terminology and Convention for Electrochemical Stripping Analysis," Technical Report, *Pure Appl. Chem*, vol. 71, No. 5, pp 891–897 (1999), month unavailable.

(List continued on next page.)

*Primary Examiner*—T. Tung
(74) *Attorney, Agent, or Firm*—Stephen A. Slusher

(57) ABSTRACT

Method and apparatus for trace metal detection and analysis using bismuth-coated electrodes and electrochemical stripping analysis. Both anodic stripping voltammetry and adsorptive stripping analysis may be employed.

24 Claims, 20 Drawing Sheets

OTHER PUBLICATIONS

Long, G.G. et al., Textbook Chapter "Bismuth and Bismuth lloys," *Encyclopedia of Chem. Technology*, M. Grayson (ed.), vol. 3, Wiley, New York, pp 921–937 (1978), month unavailable.

Nolan, M.A., et al., "Microfabricated Array of Iridium Microdisks as a Substrate for Direct Determination of $CU^{2+}$ or $Hg^{2+}$ Using Square–Wave Anodic Stripping Voltammetry," *Anal. Chem.*, vol. 71, pp 3567–3573 (1999), month unavailable.

Sun, H., et al., "Interactions of Bismuth Complexes with Metallothionein(II)," *J. of Biol. Chem*, vol. 274, No. 41, pp 29092–29101 (Oct. 8 1999).

Tallefert, M., et al., "The Application of Electrochemical Tools for *In Situ* Measurements in Aquatic Systems," *Electroanalysis*, vol. 12, No. 6, pp 401–412 (2000), month unavailable.

Wang, J., et al., "Insights into the Anodic Stripping Voltammetric Behavior of Bismuth Film Electrodoes," *Analytica Chimica Acta*, vol. 21067, pp 1–6 (2001), month unavailable.

Wang, J. et al., "Bismuth Film Electrodes for Adsorptive Stripping Voltammetry of Trace Nickel," *Electrochem. Comm.*, vol. 2, pp 390–393 (2000), month unavailable.

Wang, J., et al., "Bismuth–Coated Screen–Printed Electrodes for Tripping Voltammetric Measurements of Trace Lead," *Electroanalysis*, vol. 13, No. 1, pp 13–16 (2001), month unavailable.

Wang, J., et al., "Bismuth–Coated Carbon Electrodes for Anodic Stripping Voltammetry," *Analytical Chemistry*, vol. 72, No. 14, pp 3218–3222 (Jul. 15 2000).

Wang, J., et al., "Mercury–Free Disposable Lead Sensors Based on Potentiometric Stripping Analysis at Gold–Coated Screen–Printed Electrodes," *Anal. Chem.*, vol. 65, pp 1529–1532 (1993), month unavailable.

Wang, J., Textbook "Stripping Analysis—Principles, Instrumentation and Applications," VCH Publishers, Inc., (1985), month unavailable index pages.

Wang, J., Textbook "Analytical Electrochemistry," VCH Publishrs, Inc. (1994), month unavailable index pages.

Zhang, X., et al., "Fabrication, Characterization, and Potential Application of Carbon Fiber Cone Nanometer–Size Electrodes," *Anal. Chem.*, vol. 68, pp 3338–3343 (1996), month unavailable.

Encyclopedia Britannic internet pages on "Electrochemistry" definition (1999), month unavailable.

Zhang, X, et al., "Cathophoresis Paint Insulated Carbon Bifre Ultramicro Disc Electrode and its Application to In Vivo Amerometric Monitoring of Quantal Secretion from Single Rat Melanotrophs," *Analytica Chimica Acta*, vol. 378, pp 135–143 (1999), month unavailable.

* cited by examiner

BISMUTH-BASED ELECTROCHEMICAL STRIPPING ANALYSIS

CROSS-REFERENCE TO RELATED APPLICATIONS

This application claims the benefit of the filing of U.S. Provisional Patent Application Ser. No. 60/203,536, entitled Methods and Apparatus for Trace Metal Testing Using Bismuth-Coated Electrodes, filed on May 10, 2000, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. DE-FG07-96ER62306 awarded by the U.S. Department of Energy.

COPYRIGHTED MATERIAL

A portion of the disclosure of this patent document contains material that is subject to copyright protection. The owner has no objection to the facsimile reproduction by anyone of the patent document or the patent disclosure, as it appears in the Patent and Trademark Office patent file or records, but otherwise reserves all copyrights whatsoever.

BACKGROUND OF THE INVENTION

1. Field of the Invention (Technical Field)

The present invention relates to methods and apparatus for detection and quantification of heavy metals utilizing bismuth-coated electrodes, which electrodes may be coated with bismuth prior to use, or may be coated with bismuth in situ in a solution including a determined amount of bismuth together with the analyte.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Electrochemical stripping analysis is a powerful electroanalytical technique for trace metal measurements (J. Wang, *Stripping Analysis*, VCH Publishers, Deerfield Beach, 1985; E. P. Achterberg, C. Braungradt, *Anal. Chim. Acta* 400(1999)381; M. Taillefert, G. W. Luther, D. B. Nuzzio, *Electroanalysis* 12(2000)401). A proper choice of the working electrode is crucial for the success of the stripping operation. Film and drop mercury electrodes have been traditionally used for achieving high sensitivity and reproducibility. Mercury electrodes can be used to detect up to four to six metals simultaneously in various matrices at concentration levels down to $10^{-10}$ M. The best analytical results have been obtained using an in situ plated mercury film (T. M. Florence, *J. Electroanal. Chem.* 27(1970)273); however this approach, like pre-plated mercury films, can result in unacceptable toxicity and other environmental considerations.

Because of the toxicity of mercury, considerable efforts have been devoted to the investigation of alternate electrode materials (E. P. Achterberg, C. Braungradt, supra: J. Wang and B. Tian, *Anal. Chem.* 65(1993)1529; M. A. Nolan, S. P. Kounaves, *Anal. Chem.* 71(1999)3567). While a wide range of non-mercury electrodes, including gold, carbon, and iridium, have been examined, the overall performance of these alternative stripping electrodes has not approached that of mercury ones.

U.S. Pat. No. 3,855,099 discloses an electrode, such as a graphite electrode, for anode stripping voltammetry in which there is a metal on the surface of the electrode. Among the metals specifically taught are bismuth and a bismuth amalgam. However, this patent only discloses use of bismuth for testing for phosphate ions, which is not a metal, and specifically states that the metal for the electrode surface must be more "noble" than the analyte element, which is to say that the metal for the electrode surface should be below the analyte element in the electromotive series. Thus U.S. Pat. No. 3,855,099 discloses only detection of a nonmetallic analyte element, phosphate ion, and does not disclose use of bismuth in the analyte solution.

U.S. Pat. No. 5,830,343 relates to electrochemical analysis using metals deposited on electrodes, and teaches detection of bismuth, but does not teach use of bismuth in the electrode coating. U.S. Pat. No. 5,460,710 teaches use of metallic electrodes, including a bismuth electrode for use in pH titrations, but does not teach use of a carbonaceous electrode coated with bismuth for detection of a metal analyte by means of electrochemical stripping analysis. U.S. Pat. No. 5,391,270 teaches a method for detection of heavy metals, including bismuth, by means of forming soluble metallic complexes by use of an iodine/iodide solution and thereafter voltammetrically determining the peak stripping current value for the metallic complex in the iodine/iodide solution.

U.S. Pat. No. 5,292,423, to the inventor herein, and U.S. Pat. No. 5,635,054 each teach methods and devices for trace metal testing using mercury-coated screen printed electrodes, and electrodes coated with other metals. However, use of bismuth-coated screen printed electrodes is not specifically disclosed in either patent.

There is a need for a non-mercury electrode that offers high-quality stripping performance similar to that of mercury electrodes, and preferably a coated electrode that permits simple in situ preparation, high sensitivity, a well defined and undistorted stripping signal, and excellent resolution, particularly of neighboring peaks. Most critically, there is a need for an electrode that is more "environmentally-friendly" and that exhibits very low toxicity, with a performance at least approaching that of mercury.

SUMMARY OF THE INVENTION (DISCLOSURE OF THE INVENTION)

The invention provides a method for analyzing metals in a solution sample, which method includes the steps of providing an electrode, electrolytically depositing a bismuth metal film on the electrode and analyzing the solution sample for metal content using electrochemical stripping analysis with the electrode. In this method, a source of bismuth may be added to the solution sample, and the bismuth metal film electrolytically deposited on the electrode in the presence of the solution sample. In an alternative embodiment, the bismuth metal film is electrolytically deposited on the electrode outside the presence of the solution sample.

The electode can be a carbon-containing electrode, and may be a glassy-carbon disk electrode, carbon-fiber microelectrode, thin-film electrode or thick-film electrode. The electrode may also be a screen-printed electrode.

The method can also include providing at least one reference electrode.

In the method, the step of analyzing the solution sample for metal content using electrochemical stripping analysis can include either stripping voltammetry or stripping potentiometry. In the case of stripping voltammetry, the method can include anodic stripping voltammetry or adsorptive stripping voltammetry.

In the method, the step of analyzing the solution sample for metal content can include use of the bismuth as an internal standard. The method can further include analyzing the solution sample for metal content to make a quantitative determination of the quantities of trace metal. Analyzing the solution sample for metal content can also include simultaneously analyzing the solution sample for more than one metal. The solution sample can be a sample of body fluid, and can also be any other fluid sample.

The invention also includes an apparatus for detection of trace metals in solution, which apparatus includes a plurality of thick-film electrodes on a substrate and a bismuth metal film on at least one of the electrodes. The apparatus can further include at least one reference electrode, including a silver-containing reference electrode on the substrate. The thick-film electrode can include carbon, and may be a screen-printed electrode. The apparatus can further include an electrochemical analyzer.

A primary object of the present invention is to provide a bismuth-based electrode for electrochemical stripping analysis.

Another object of the invention is to provide an apparatus and method whereby an electrode may be coated in situ with bismuth.

Another object of the invention is to provide a bismuth-coated electrode detection system for detection of metals, including but not limited to lead, cadmium, zinc, copper, indium, thallium and nickel.

Another object of the invention is to provide a bismuth-coated electrode detection system for quantitative detection and determination of metals.

Another object of the invention is to provide a bismuth-coated screen-printed electrode.

Yet another object of the invention is to provide a bismuth-coated electrode for simultaneous detection and analysis of more than one metal.

A primary advantage of the present invention is the decreased toxicity and improved environmental safety using bismuth-based electrodes as compared to mercury-based electrodes.

Another advantage of the invention is the low cost of bismuth-based electrodes for metal detection.

Another advantage of the invention is that bismuth-based electrodes may be safely disposed of without adverse environmental considerations.

A further advantage of the invention is the highly stable and reproducible response of bismuth-based electrodes.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
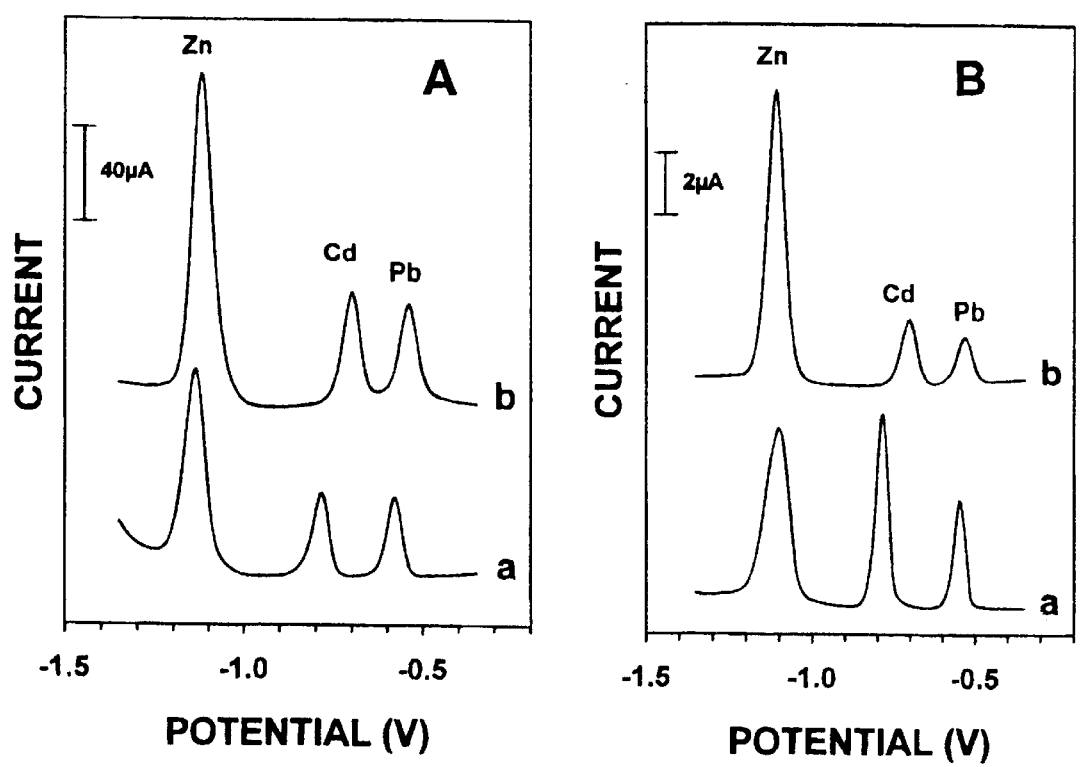
FIG. 1 are stripping voltammograms of lead, cadmium and zinc at a glassy carbon (A) and carbon fiber (B) electrode coated with bismuth (a) or mercury (b) films.

DESCRIPTION OF THE PREFERRED EMBODIMENTS (BEST MODES FOR CARRYING OUT THE INVENTION)

The invention includes electrodes that are coated or plated with a bismuth-containing film prior to use, and the electrode may thereafter be dried and stored until use. In the embodiment with bismuth coated or plated electrodes, the analyte solution does not include bismuth. The bismuth-coated electrodes can be carbon fiber or glassy carbon electrodes, or can be any other form of electrode, including generally any conductive material, including but not limited to flat, screen-printed carbon electrodes. Accordingly, the disclosure of U.S. Pat. No. 5,292,423 is incorporated by reference, it being understood that the electrodes of U.S. Pat. No. 5,292,423 may be employed, and coated with bismuth utilizing the same general methods described therein for coating with mercury. Further, both thin-layer and thick-layer electrodes may be employed in the practice of this invention, both either coated or plated with a composition including bismuth, or alternatively using an analyte solution that includes bismuth. The electrode may include any base material or substrate, including polymeric materials, ceramics and the like.

The invention further includes use of any of a wide variety of carbonaceous electrodes, including but not limited to carbon paste electrodes, glassy carbon electrodes, bare carbon electrodes, reticulated carbon electrodes, and the like. Additionally, any conducting electrode, including metallic electrodes such as gold or iridium electrodes, may be used in the practice of this invention, including both bismuth coated or plated conducting electrodes and conducting electrodes wherein the analyte solution includes bismuth.

The invention further includes a method of analysis in which the target metal analyte and bismuth are co-deposited on the electrode, such as by coating or plating. Thus a solution including bismuth and the analyte are coated or plated on the electrode, and thereafter analysis performed.

The invention further includes use of different forms of bismuth. Thus solid bismuth may be employed, and preferably in particulate or granular form. Similarly, bismuth salts may be employed as the active electrode materials. In one embodiment, solid bismuth or bismuth salts are employed in a paste, gel or polymeric material which is coated or plated on the electrode prior to use.

The invention may be employed for any application in which heavy metal detection is desired, including but not limited to medical applications, such as determination of heavy metal concentrations in blood, sera and other fluids, environmental applications, such as determination of heavy metal contaminants in water or soil, food industry applications, and industrial applications, such as determination of concentrations of heavy metals in solutions, waste discharge, and the like. The invention may further be employed in remote sensing of heavy metals in harsh environments, such as generally disclosed in U.S. Pat. No. 5,676,820, incorporated by reference.

Figure 2:
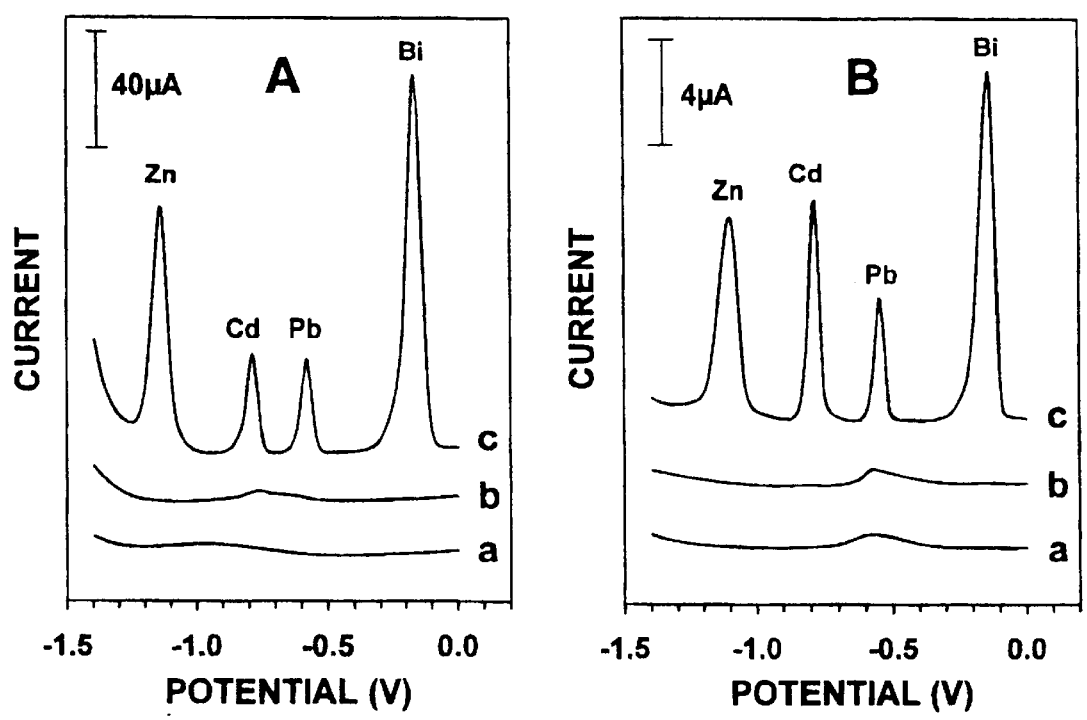
FIG. 2 are stripping voltammograms at glassy carbon (A) and carbon fiber (B) electrodes.

The bismuth peak, appearing at approximately −0.2 V on FIG. 2, may further be utilized as an internal standard, to validate and calibrate the function of the apparatus and proper performance of the method, and to provide a quantification reference, the amount of bismuth in solution or coated on the electrode being known, such that the peak height may be predicted based on known quantities, and the measurements accordingly adjusted to such known quantities.

The invention may further be employed for adsorptive stripping analysis, which results in increased sensitivity and measurement of additional analytes. In this method, either bismuth coated or plated electrodes of this invention may be employed, or the bismuth may be in the solution to be analyzed. This method involves the formation, adsorptive accumulation and reduction of a surface-active complex of a trace metal. Any appropriate chelating agent or ligand may be employed. This approach increases the sensitivity of detection, permitting extremely low level detection for many metals. This approach also increases selectivity for metals compared to standard methods. In addition, adsorptive stripping may also be employed for measuring organic compounds using the bismuth electrodes of this invention. The disclosure in *Analytical Electrochemistry* by Joseph Wang, VCH Publishers, Inc., New York, 1994, is incorporated herein by reference.

For embodiments wherein the electrode is coated with bismuth prior to use, any suitable electrode, preferably a carbon-containing electrode, may be employed. Carbon-containing or carbon-substrate electrodes include glassy-carbon disk electrodes, carbon-fiber microelectrodes, thick-film electrodes, such as screen-printed electrodes made using a carbon-ink, thin-film electrodes and the like. The electrode may be of any size; typically a glassy-carbon disk electrode will have a working surface diameter from about 1.0 to about 5.0 mm, a carbon-fiber microelectrode will be approximately 1 mm in length and approximately 7 μm in diameter, and so on. Thin-film and screen-printed thick-film electrode working surfaces may be any convenient size, such as from a width of about 1 mm to about 5 mm, and a length from about 1 mm to about 10 mm. Other conducting electrodes may be employed, including electrodes made from a metal.

In all embodiments, there may be provided a reference electrode and a counter electrode. The reference electrode may conveniently be an Ag/AgCl wire, and the counter electrode may conveniently be a platinum wire. However, the reference and counter electrodes may be made from any suitable material, and may be in any desired shape or configuration.

To coat the electrode with bismuth, cathodic accumulation may be employed. In one embodiment, a set quantity of bismuth is employed, such as about 500 μg/L to about 1000 mg/L bismuth, in the form of bismuth (III), in a suitable buffer. The buffer may be any suitable supporting electrolyte buffer such as an acetate buffer. The bismuth may be obtained in any soluble or solubilizable form, including conveniently in an acid-containing solution, such as a 5% nitric acid solution. Any form of cathodic accumulation may be employed, such as application of a potential from about −0.5 V to about −2.0 V for from about 1 to about 10 minutes. However, the applied potential and deposition time may be varied from these parameters, and the user may easily ascertain operable parameters by empirical means.

Once the electrode has been coated, the electrode may be dried and stored until used. The electrode may be incorporated into any desired device or apparatus, including devices for analysis of body fluids, including blood and urine, analysis of environmental fluids, including water, waste streams, and the like, and for analysis of other fluids, including process analysis in manufacturing applications.

Analysis may be by any means of electrochemical analysis. In one embodiment, anodic stripping voltammetry is employed. This may be, for example, by application of a positive-going square-wave potential scan. However, other forms of electrochemical analysis may be employed, including stripping potentiometry, stripping chronopotentiometry, cathodic stripping voltammetry, and adsorptive stripping voltammetry. For stripping voltammetry, any of a variety of waveforms can be employed, including square wave stripping voltammetry, linear sweep stripping voltammetry, differential pulse cathodic stripping voltammetry, and square wave adsorptive stripping voltammetry.

While cathodic accumulation is generally employed for bismuth coating, other forms of accumulation may be employed. These include, in addition to cathodic accumulation, anodic accumulation and adsorptive accumulation, as well as a combination of either cathodic or anodic with adsorptive accumulation.

It is also intended and contemplated that bismuth may be accumulated concurrently with one or more substances to be analyzed, such as trace metals. In this embodiment, a suitable quantity of bismuth is added to the solution to be analyzed, such as from about 500 $\mu$g/L to about 1000 mg/L of bismuth in a suitable form, such as bismuth (III). The accumulation of bismuth in situ together with substances to be analyzed may be accomplished by any of the accumulation means discussed above, including cathodic accumulation. Any suitable deposition potential and time may be employed. Where bismuth is accumulated concurrently with one or more substances to be analyzed, any form of electrochemical analysis may be employed, as discussed above.

Industrial Applicability

The invention is further illustrated by the following non-limiting examples.

EXAMPLE 1

Stripping voltammetry was performed using a BAS CV-50W voltammetric analyzer (Bioanalytical Systems). A bismuth or mercury-coated glassy-carbon (GC) disk (3 mm diameter) or carbon fiber microelectrode (CFME) served as the working electrode, with an Ag/AgCl (3 M NaCl) and platinum wire acting as the reference and counter electrodes, respectively. Solutions were prepared with doubledistilled water. Standard stock solutions of bismuth, mercury, copper, gallium, indium, thallium, cadmium, lead, and zinc (1000 mg/L, Atomic Absorption Standard solution) were obtained from Aldrich and diluted as required. A 0.1 M sodium acetate buffer solution (pH 4.5) served as the supporting electrolyte.

EXAMPLE 2

Preparation of a CFME is described generally in X. Zhang, B. Ogorevc, M. Rupnik, M. Kreft, R. Zorec, *Anal Chim. Acta*, 378(1999)135 and X. Zhang, W. Zhang, X. Zhou, B. Ogorevc, *Anal. Chem.*, 68(1996)3338. A cleaned single carbon fiber (7 $\mu$m in diameter, 2–3 cm in length, Goodfellow Co., Oxford, UK) was attached to a copper wire using silver paint (SPI Supplies, West Chester, Pa.) and inserted into glass capillary tube (7 $\mu$m in length, Euroglass, Ljubliana, Slovenia). Employing a fine pulling technique, as described in H. Z. Sun, H. Y. Li, P. J. Sadler, *J. Biolog. Chem.* 274(1999)29094, the carbon fiber was directly sealed by pulling the glass capillary tube using a microelectrode puller. Prior to the pulling, the copper wire was fixed at the stem end of the capillary tube by casting a drop of nonconducting epoxy resin. The exposed carbon fiber was then cut to a length of approximately 1 mm using a microsurgical scalpel blade. The resulting CFMEs were inspected electrochemically, in 1 mM ferricyanide solution, and optically using an inverted microscope. The selected CFMEs were stored in tightly closed boxes prior to their stripping application use.

EXAMPLE 3

Stripping voltammetric measurements were performed by in situ deposition of a bismuth film (or control mercury film) and the target metals in the presence of dissolved oxygen. Prior to use, the GC electrode of Example 1 was polished with 0.05 $\mu$m alumina slurry on a felt pad. The GC electrode and reference and counter electrodes were immersed into either a 10 mL or 15 mL electrochemical cell, containing 0.1 M acetate buffer at pH 4.5 and either 400 or 500 $\mu$g/L of bismuth or 1000 $\mu$g/L mercury. The deposition potential, selected in accordance to the target metals, was applied to the GC electrode, while the solution was stirred. Following the preconcentration or accumulation step (usually 120 seconds), the stirring was stopped and after 10 seconds, the voltammogram was recorded by applying a positive-going square-wave potential scan, with a frequency of 20 Hz, amplitude of 25 mV and potential step of 5 mV. The scan was terminated at 0.0 V (Cd, Zn, Pb) +0.3 (Bi) or +0.5 (Hg) V. Aliquots of the target metal standard solution were introduced after recording the background voltammograms. A 30-second conditioning step at +0.3 or +0.5 V (with solution stirring) was used to remove the target metals and the bismuth (or mercury) films prior to the next cycle.

EXAMPLE 4

FIG. 1 illustrates typical anodic stripping voltammograms for some common ions, present at the 50 ppb ($\mu$g/L) level, obtained at bismuth-(a) and mercury-(b) coated GC electrodes (A) and CFME (B). The electrodes of Examples 1 and 2, with the methods of Example 3, were employed. The analyte solution was 0.1 M acetate buffer at pH 4.5, containing 50 $\mu$g/L of lead (II), cadmium (II), and zinc (II), along with 400 $\mu$g/L bismuth (for "a") or 10 mg/L mercury (for "b"). Deposition was for 120 seconds at −1.4 V. Both electrodes display well-defined, sharp (nearly symmetrical) and separated peaks following the 2 minute deposition. While the zinc and lead peak potentials are nearly identical for the bismuth and mercury electrodes, the cadmium peak for the bismuth electrode appears at a more negative potential (−0.79 V vs. −0.70 V at the mercury surface). The peak sharpness was not compromised using the bismuth electrode, with peak half widths of 26 and 35 mV for Cd and Zn at the bismuth-coated GC electrode, vs. 30 and 34 mV, respectively, at the corresponding mercury film. The bismuth-plated CFME displayed higher sensitivity for lead and cadmium, compared to the mercury-coated CFME, but a lower zinc response. The square-wave voltammetric scan resulted in a low nearly flat background current in the presence of dissolved oxygen. With the exception of a slightly higher hydrogen-evolution background contribution (at approximately −1.2 V), the bismuth electrode displayed a similar background current compared to the mercury electrode.

EXAMPLE 5

The stripping performance of the bismuth-film electrodes of Example 1 and 2, using the methods of Example 3, is illustrated in the stripping voltammograms of FIG. 2, which also show the corresponding control bare-electrode experiments. No stripping signals were observed at the bare GC electrode (A(a)) and CFME (B(a)) for a sample containing only 0.1 M acetate buffer at pH 4.5 or containing 50 $\mu$g/L lead (II), cadmium (II) and zinc (II) in the buffer at the bare GC electrode (A(b)) and CFME (B(b)). Adding 400 $\mu$g/L bismuth to the sample containing 50 $\mu$g/L each of lead (II), cadmium (II) and zinc (II) resulted in the appearance of sharp and undistorted stripping peaks for all metals, including bismuth, at the GC electrode (A(c)) and CFME (B(c)).

EXAMPLE 6

Scanning electron micrographs were obtained at 1000 and 5000 magnification of typical regions of CFME and GC electrodes of Examples 1 and 2 both before and after bismuth deposition. Deposition was for 10 minutes at −1.2 V utilizing an acetate buffer solution at pH 4.5 containing 50 mg/L bismuth, with a 20 kV accelerating voltage. Different surface morphologies were observed on the carbon substrates. The scanning electron microscopy (SEM) image of the bismuth-coated GC electrode showed a highly porous, three-dimensional fibril-like network. A thick, quite uniform, non-porous bismuth deposit was observed on the CFME. The substantial increase of the fiber diameter (from 7 to about 35 $\mu$m) demonstrated significant bismuth deposition.

EXAMPLE 7

Figure 3:
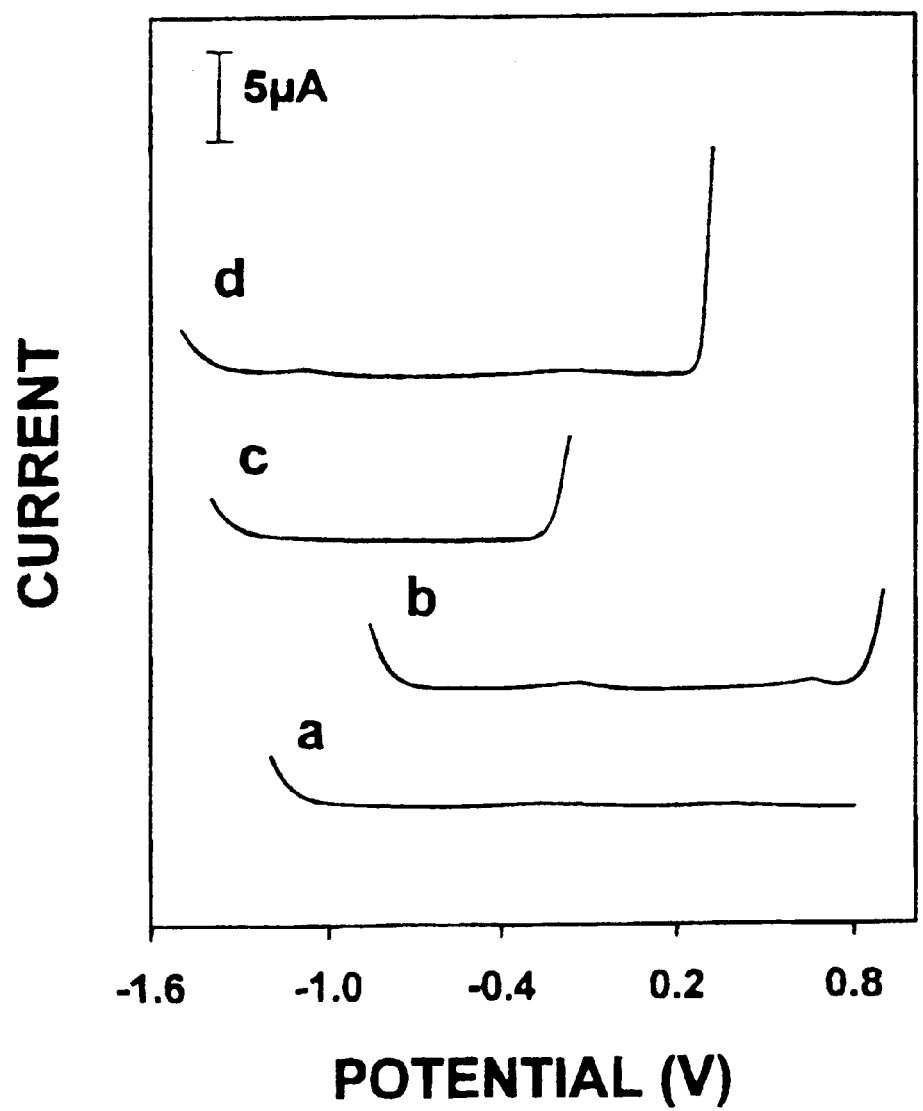
FIG. 3 is a graph depicting the accessible potential windows of carbon fiber electrodes coated with gold films (b), bismuth films (c) and mercury films (d), with a bare carbon fiber electrode (a) for comparison.

FIG. 3 depicts the accessible potential window of CFMEs of Example 2 coated with different films, including gold (b), bismuth (c) and mercury (d), using an acetate buffer as in Example 3, with a bare carbon CFME as reference (a). The bare carbon (a) and gold (b) electrodes exhibit a wide anodic potential window (>0.80 V) with a limited cathodic range (up to −1.0 V and −0.70 V, respectively). The mercury-coated carbon electrode (d) exhibits a high hydrogen overvoltage (in the vicinity of −1.30 V) with a limited anodic range due to the oxidation of mercury. The bismuth-coated electrode (c) exhibits a limited anodic region, presumptively due to bismuth oxidation, in the vicinity of −0.2 V, and an extended cathodic potential range (at approximately −1.20 V). With a potential window of around 1.0 V, five to six stripping peaks may be observed simultaneously using the bismuth-coated CFME. The bismuth-coated electrode is readily applicable for measurements of electrolytically-deposited elements with standard potentials more negative than bismuth.

EXAMPLE 8

Figure 4:
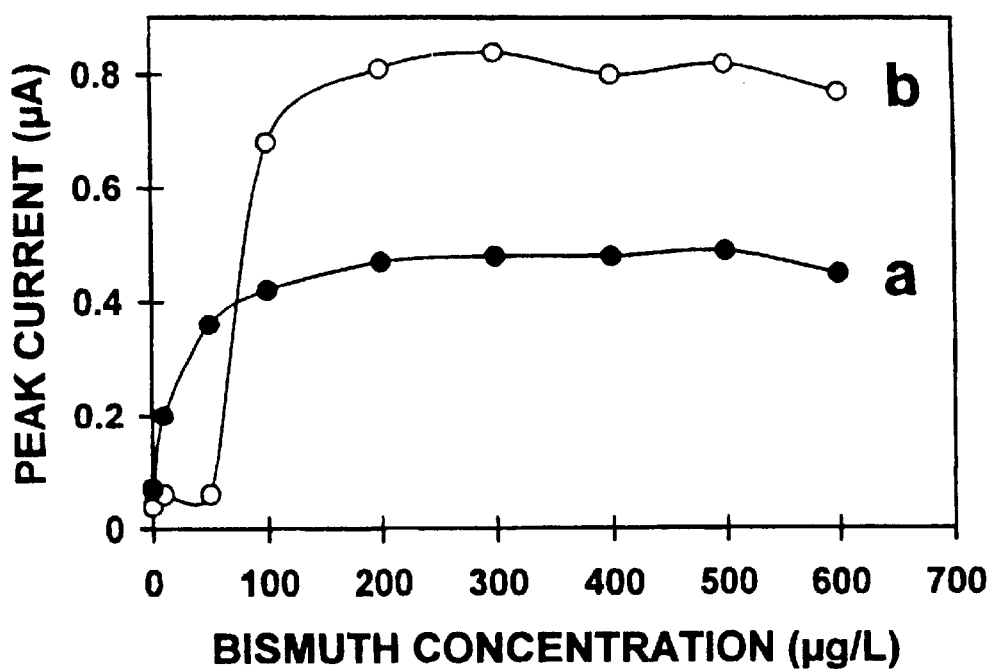
FIG. 4 is a graph depicting the effect of bismuth concentration on the stripping voltammetric response of lead (II) and cadmium (II)

The effect of bismuth ion concentration upon the resulting stripping response is shown in FIG. 4. Using the methods of Example 3, with deposition for 120 seconds at −1.2 V and 100 $\mu$g/L of lead (a) or cadmium (b), both the lead (a) and cadmium (b) peaks increase rapidly upon raising the bismuth concentration from 50 to 100 $\mu$g/L, and level off above 200 $\mu$g/L. The different trends observed for cadmium and lead below 50 $\mu$g/L bismuth were attributed to different standard potentials. A low bismuth coverage was sufficient for depositing the more easily reduced lead ion. A bismuth concentration of 400 $\mu$g/L was used for most subsequent analytical work. Mercury levels higher than 400 $\mu$g/L ($2\times10^{-6}$ M) are required for the successful use of in situ plating of mercury film electrodes.

EXAMPLE 9

Figure 5:
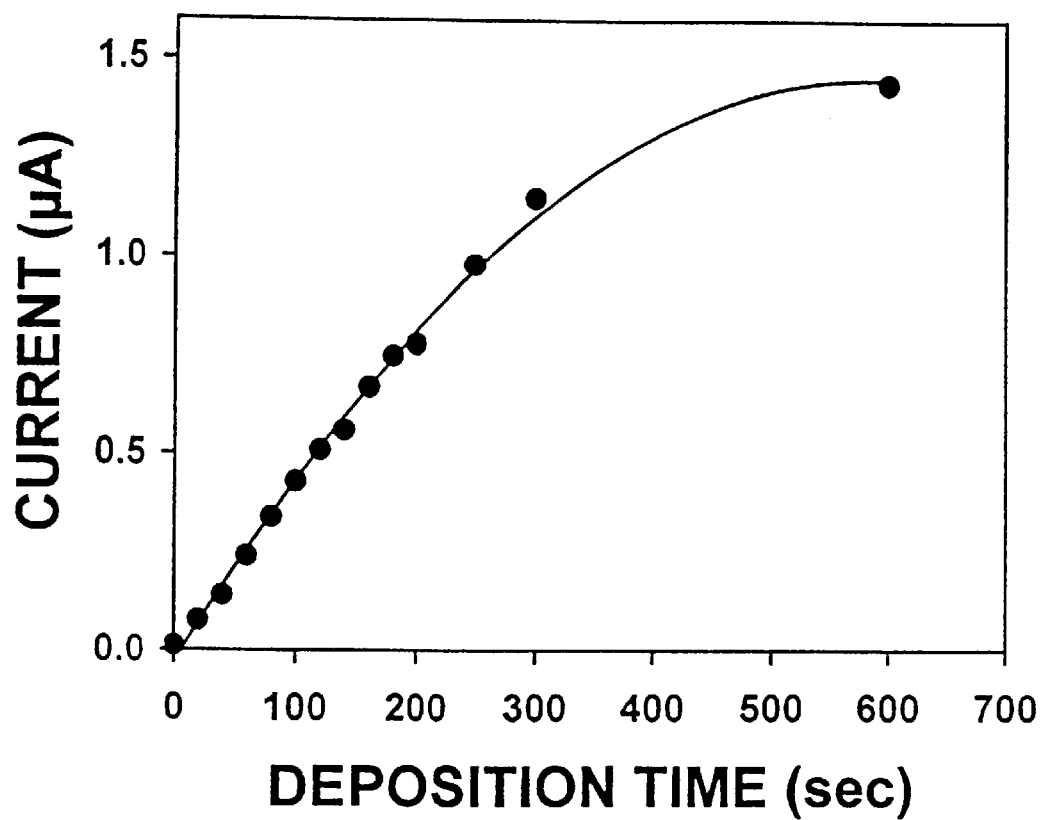
FIG. 5 is a graph of the pre-concentration time upon the stripping voltammetric response of lead (II)

FIG. 5 depicts the effect of the pre-concentration or deposition time upon the stripping voltammetric response of 120 $\mu$g/L lead (II), utilizing a deposition potential of −1.2 V. The peak increases linearly with the pre-concentration time at first, for up to 3 minutes, then more slowly, and starts to level off above 5 minutes. Very short accumulation periods, of 30–60 seconds, are thus sufficient for obtaining favorable signal-to-background characteristics for $\mu$g/L concentrations of heavy metals. While the leveling off observed at longer periods can be attributed to surface saturation, no multiple or broader peaks were observed under these conditions.

EXAMPLE 10

Figure 6:
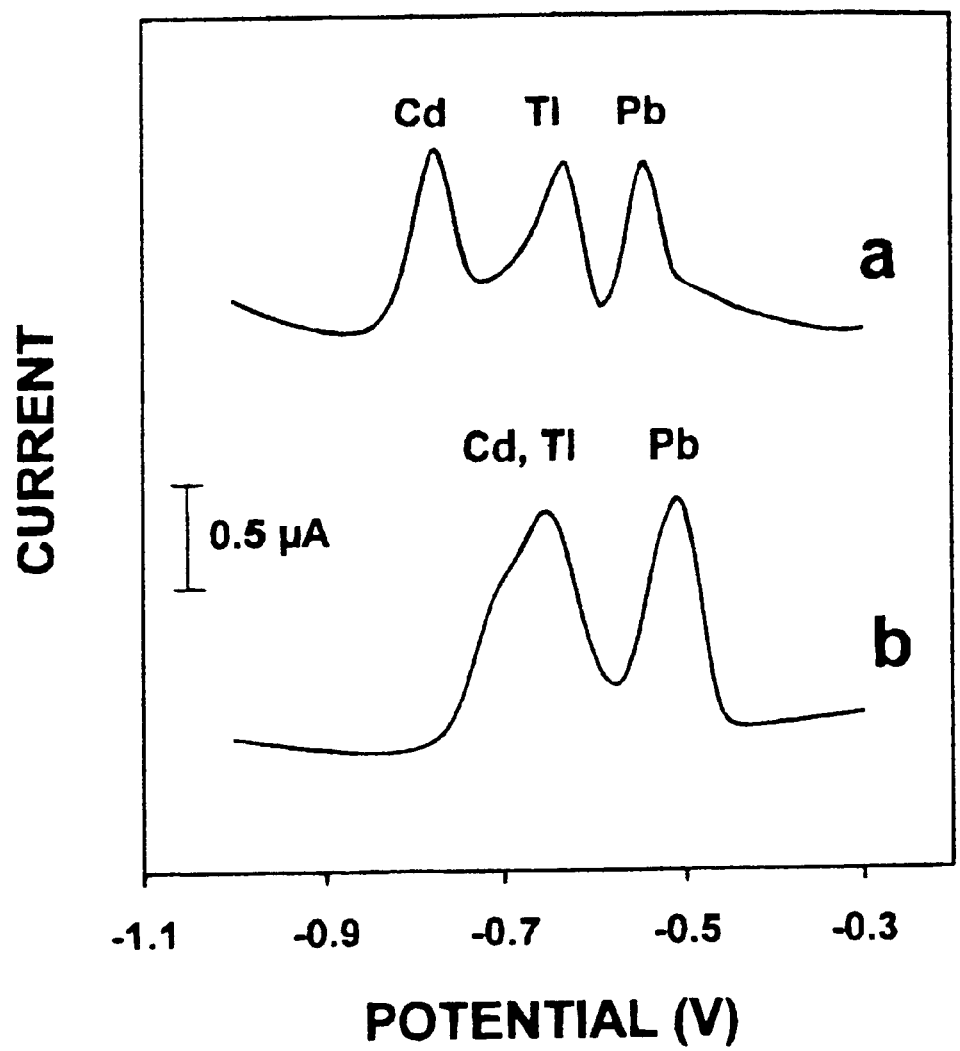
FIG. 6 are stripping voltammograms of lead, cadmium and thallium at bismuth (a) and mercury (b) thin-film electrodes.

The different stripping potentials observed at the bismuth-coated electrode permit selectivity not possible with mercury electrodes. The quantitation of thallium in the presence of cadmium and lead is a common problem in mercury electrode stripping voltammetry due to overlapping stripping signals. This resolution problem is shown in FIG. 6, where the thallium peak is obscured by an overlapping cadmium peak at the mercury thin-film electrode (b). In contrast, the bismuth thin-film electrode (a) resulted in separated peaks, permitting quantitation of the three metal ions. The stripping voltammograms of FIG. 6 show 50 $\mu$g/L each of lead (II), cadmium (II) and thallium (II) at bismuth (a) and mercury (b) thin-film electrodes, utilizing a 0.1 M acetate buffer at pH 4.5 containing 400 $\mu$g/L bismuth (a) or 10 mg/L mercury (b), with deposition for 120 seconds at −1.2 V.

EXAMPLE 11

Figure 7:
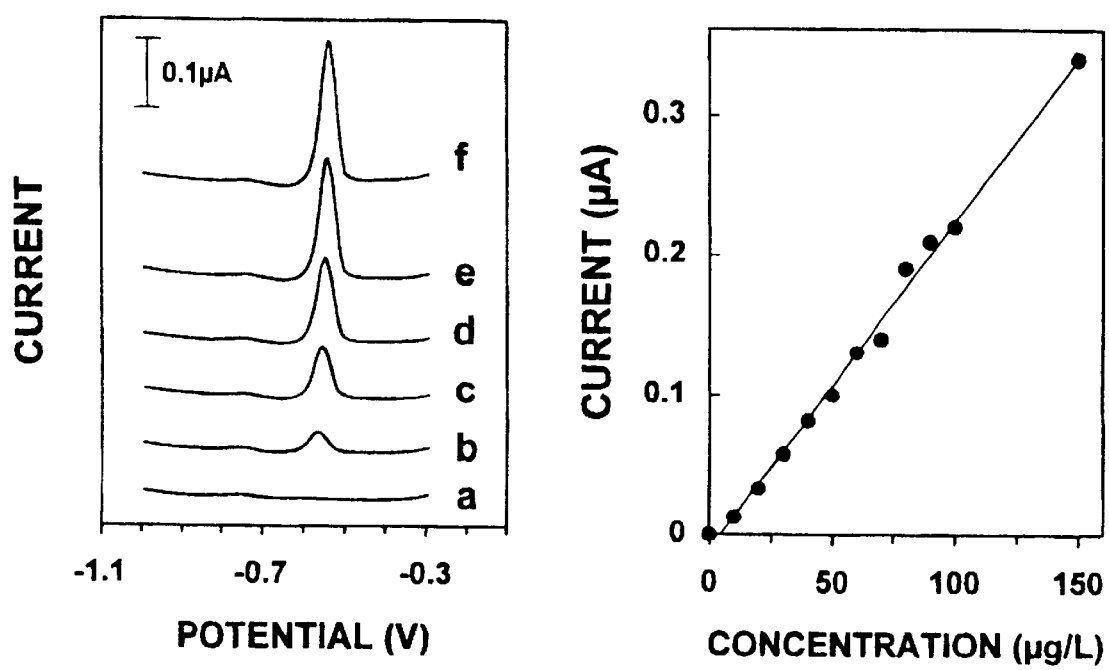
FIG. 7 are stripping voltammograms for increasing levels of lead (II)

FIG. 7 displays stripping voltammograms obtained upon increasing the lead (II) concentration in 20 $\mu$g/L steps (b–f together with the background response (a). Well-defined sharp peaks, over a flat baseline, were observed following the 2-minute deposition. The five measurements shown are part of a series of eleven concentration increments up to 150 $\mu$g/L lead. The resulting calibration plot is linear over the entire range (slope, 0.0023 $\mu$A.L/$\mu$g; correlation coefficient, 0.995). The signal-to-noise (S/N) characteristics of the 10 $\mu$g/L data point was used to estimate the detection limit (1.1 $\mu$g/L lead; S/N=3). A longer deposition period of 10 minutes further enhanced the S/N characteristics, with a detection limit of 0.3 $\mu$g/L ($1.4\times10^{-9}$ M) lead based on measurements of a 5 $\mu$g/L lead solution.

EXAMPLE 12

A series of 22 repetitive measurements of a solution containing 80 $\mu$g/L lead and cadmium resulted in highly reproducible stripping peaks, with relative standard deviations of 4.4% and 2.4% respectively, utilizing a 2 minute deposition at −1.2 V. This precision is attributed to the reproducible film renewal accrued from the in situ bismuth plating. Compared to the "stabilization" period required for in situ plating of mercury film electrodes, bismuth coated electrodes display a highly stable response starting with the first run.

EXAMPLE 13

Figure 8:
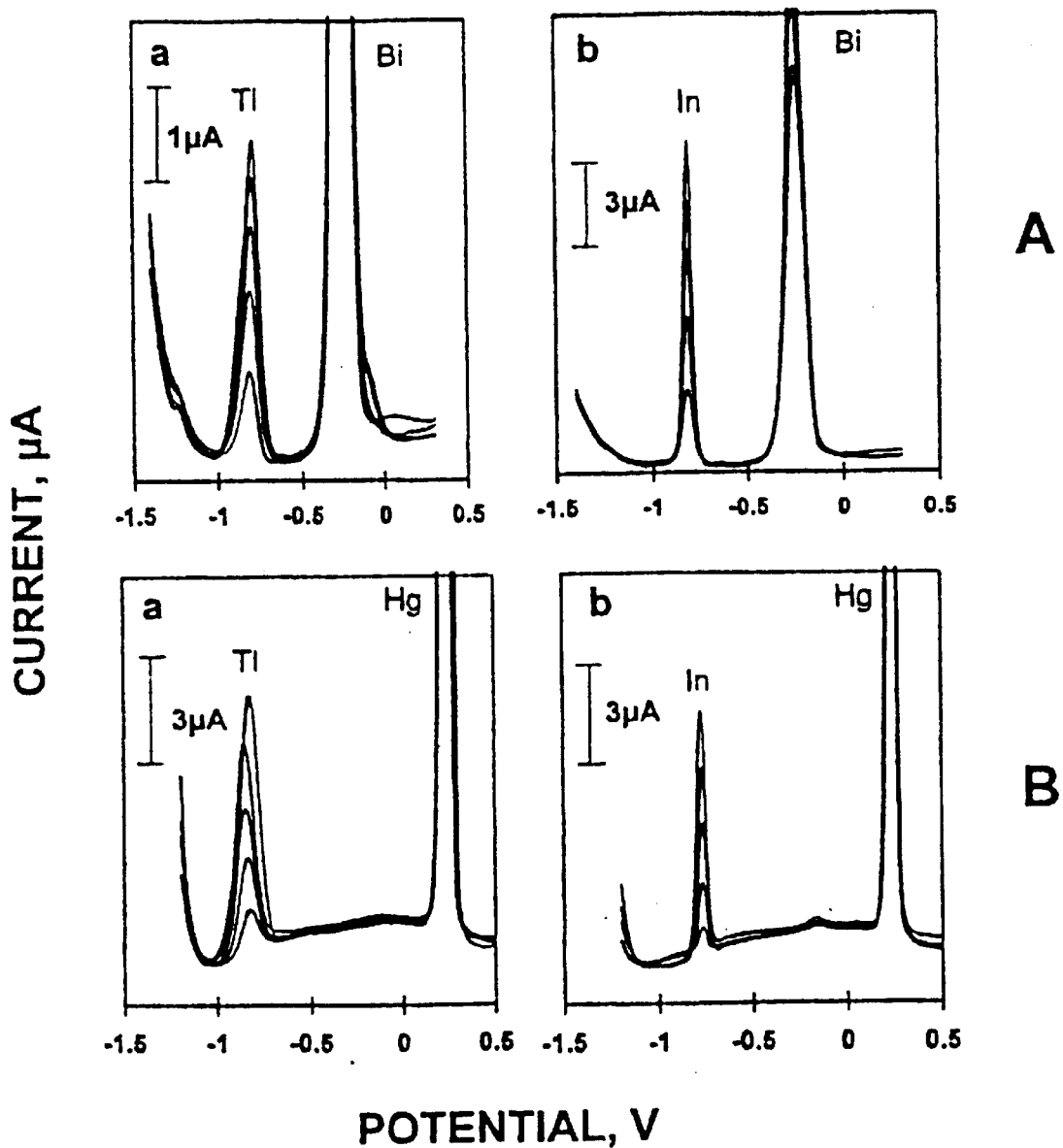
FIG. 8 are stripping voltammograms at bismuth (A) and mercury (B) coated glassy-carbon electrodes for thallium (a) and indium (b) solutions of increasing concentrations in 20 $\mu$g/L steps.

FIG. 8 depicts square-wave stripping voltammograms obtained at bismuth (A) and mercury (B) coated GC electrodes for solutions of increasing thallium (a) and indium (b) concentrations (20–200 µg/L (ppb)) after a 120 second deposition. Parameters were as in Example 3, with the acetate buffer containing 500 µg/L bismuth, and with a 30 second condition step at +0.3 V for bismuth and +0.5 V for mercury. The bismuth film electrode displayed well-defined and undistorted single and sharp peaks for both metals [$E_p$=−0.79 V (Tl) and −0.81 V (In)], which are surrounded by a low background current. The resulting calibration plots was linear, with sensitivities of 35 (A,a) and 103 (A,b) nA.L/µg. The mercury electrode displayed a higher sensitivity towards thallium (75 nA.L/µg) and a lower one (81 nA.L/µg) towards indium. The overall signal-to-background characteristics of the bismuth electrode compare favorably with those observed at the mercury counterpart. A detection limit of around 4 and 2 µg/L of thallium and indium, respectively can be estimated from the signal-to-noise characteristics of the data (S/N=3), with lower detection limits for longer deposition periods. The data of FIG. 8 further show that the bismuth-film electrode can be used for measurements of electroplated elements with standard potentials more negative than bismuth.

EXAMPLE 14

Figure 9:
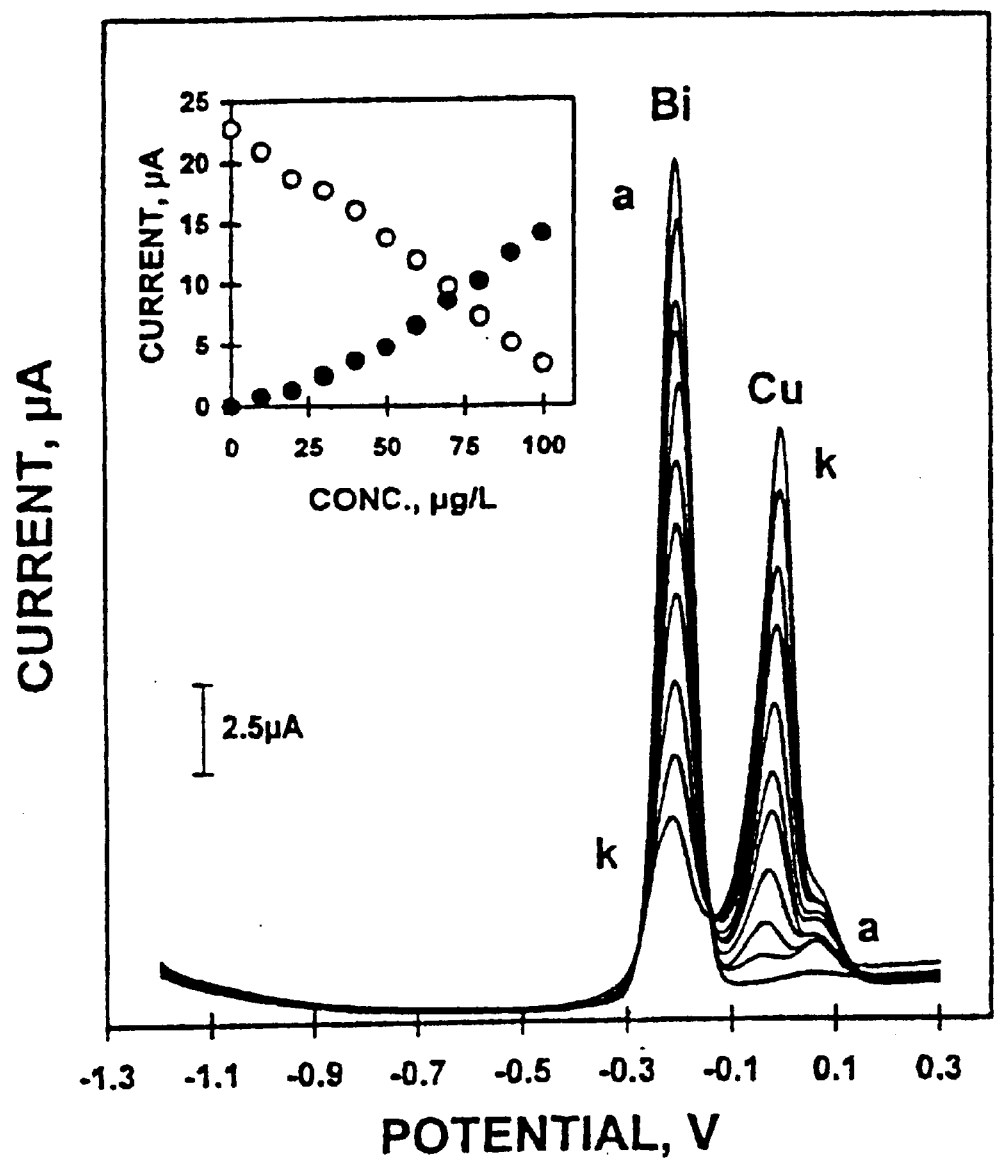
FIG. 9 are stripping voltammograms at a bismuth-coated glassy-carbon electrode for copper solutions of increasing concentrations in 10 $\mu$g/L steps (a–k)

FIG. 9 shows the stripping voltammetric response of the bismuth-coated GC electrode for 10 successive concentration increments of 10 µg/L copper (a–k), utilizing the methods of Example 3. While a split or dual copper signal is observed at low (10–20 µg/L) levels of the metal, higher concentrations display mostly sharp copper peaks (at ca. −0.02 V), with only a small shoulder at +0.06 V. Similar distorted copper signals are often observed at mercury film electrodes. The calibration plot in FIG. 9 is linear above 20 µg/L (copper (•) and bismuth (O)), with a slight curvature at lower levels associated with the appearance of the shoulder. A detection limit of around 5 µg/L copper can be estimated from the signal-to-noise characteristics of these data (S/N= 3). The copper response at the bismuth electrode is highly reproducible, with a series of 12 repetitive measurements of 40 µg/L copper yielding a relative standard deviation of 2.0%, with a mean peak current of 2.6 µA. The copper signal, as well as the bismuth peak, increased linearly with the deposition time over a 1–5 minute range.

EXAMPLE 15

Figure 10:
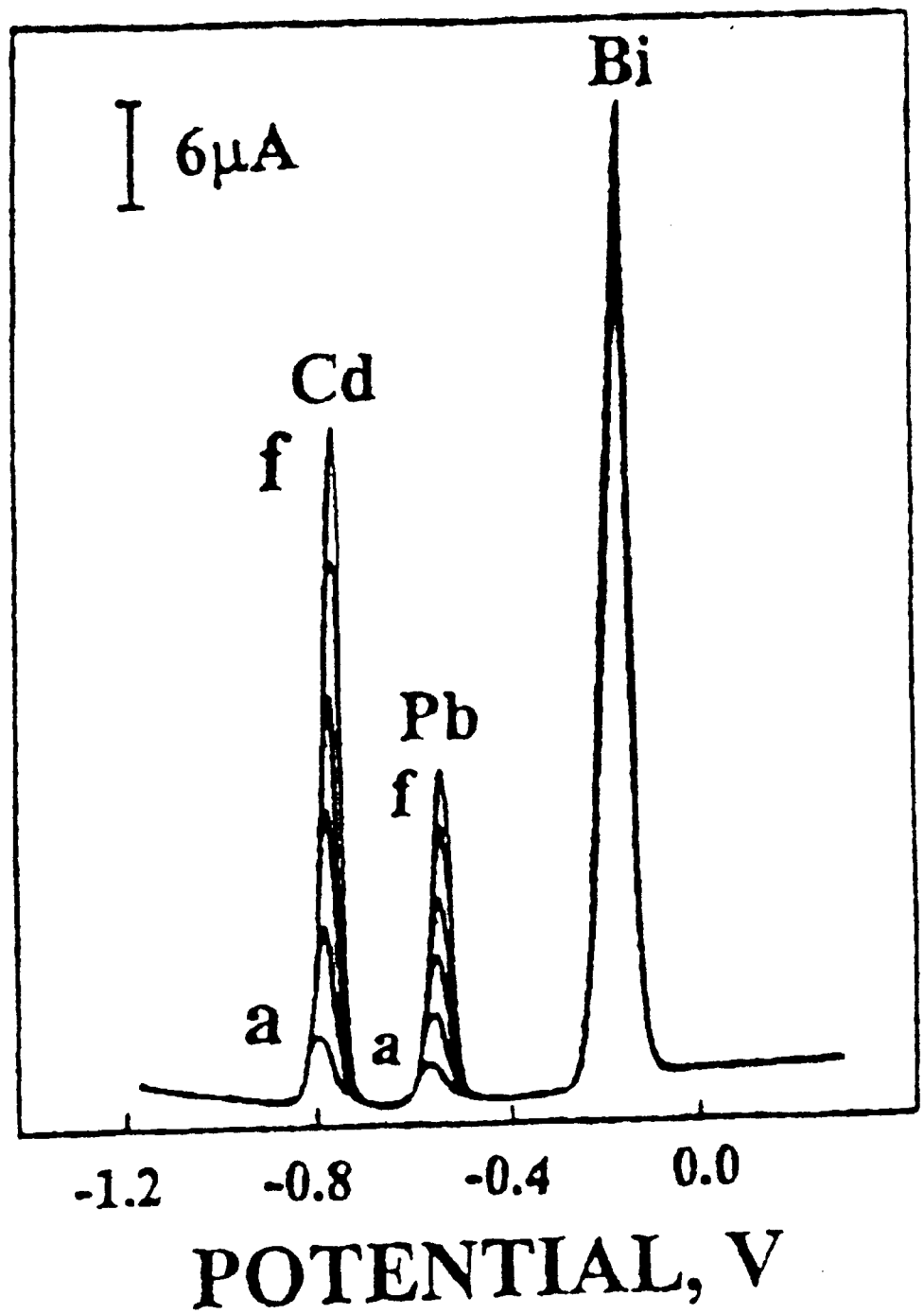
FIG. 10 are square-wave stripping voltammograms of detection of increasing concentrations of lead and cadmium in 20 $\mu$g/L steps.

Stripping behavior of copper at the bismuth-coated GC electrode is different from that of lead or cadmium. FIG. 10 shows that increasing levels of these metals in 20 µg/L steps has no effect upon the bismuth peak. Apparently, neither cadmium nor lead compete with the bismuth for the surface site, but rather form a binary alloy with bismuth. It is well known that bismuth forms binary or multi-component "fusing" alloys with lead, cadmium, thallium, and indium (G. G. Long, L. D. Freedman, G. O. Doak, "Bismuth and bismuth alloys", in *Encyclopedia of Chemical Technology*, M. Grayson (Ed.), Vol. 3, Wiley, New York, 1978, pp. 912–937). Such alloy formation appears to be responsible for the attractive and unique stripping performance of bismuth-coated electrodes. The similar stripping behavior observed in FIG. 8 for thallium and indium, with a negligible effect upon the bismuth peak, indicates that these metals also form binary alloys with bismuth. In FIG. 10 well-defined and undistorted lead and cadmium signals increase linearly with the metal concentration. Such behavior reflects the attractive stripping performance of the bismuth film electrode.

EXAMPLE 16

Figure 11:
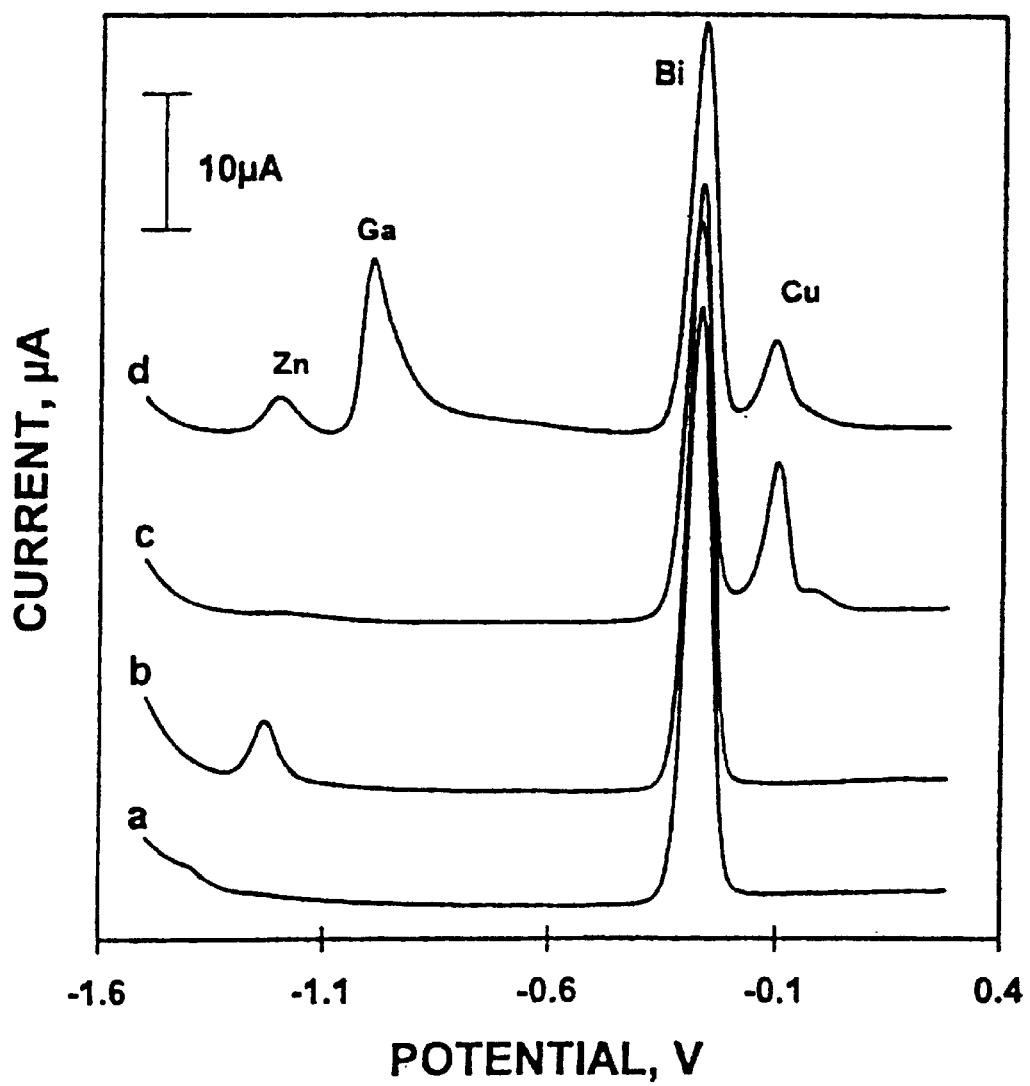
FIG. 11 are square-wave stripping voltammograms for detection of (a) 500 $\mu$g/L bismuth, (b), 200 $\mu$g/L zinc, (c) 100 $\mu$g/L copper and (d) 1000 $\mu$g/L gallium, each in 0.1 M acetate buffer solution.

An inherent problem in stripping voltammetry is the potential interaction between metals that have been co-deposited onto the electrode surface (J. Wang, *Stripping Analysis*, VCH Publishers, Deerfield Beach, 1985; J. A. Wise, D. A. Roston, W. R. Heineman, *Anal. Chim. Acta*, 154(1983)95). Stripping voltammetry at mercury-film electrodes is prone to errors associated with the formation of Cu—Zn compounds. Similar results were observed as shown in FIG. 11 using a bismuth-coated GC electrode, utilizing a 0.1 M acetate buffer solution containing 500 µg/L bismuth (a), the addition of 200 µg/L zinc (b); the addition of 100 µg/L copper (c), and the addition of 1000 µg/L gallium (d). The well-defined zinc peak, observed in the absence of copper (b) was fully suppressed in the presence of 100 µg/L copper (c). FIG. 11(d) illustrates that the addition of 1 mg/L gallium restored a well-defined zinc peak, thereby obviating the apparent Cu—Zn intermetallic formation at the bismuth-coated GC electrode. FIG. 11(d) also depicts a large gallium peak, which does not affect the restored zinc signal, and a high hydrogen overvoltage of around −1.5 V. It is also possible to mask the copper in the solution, via selective complexation using known complexing agents, and thereby prevent Cu/Bi competition for surface sites.

EXAMPLE 17

Figure 12:
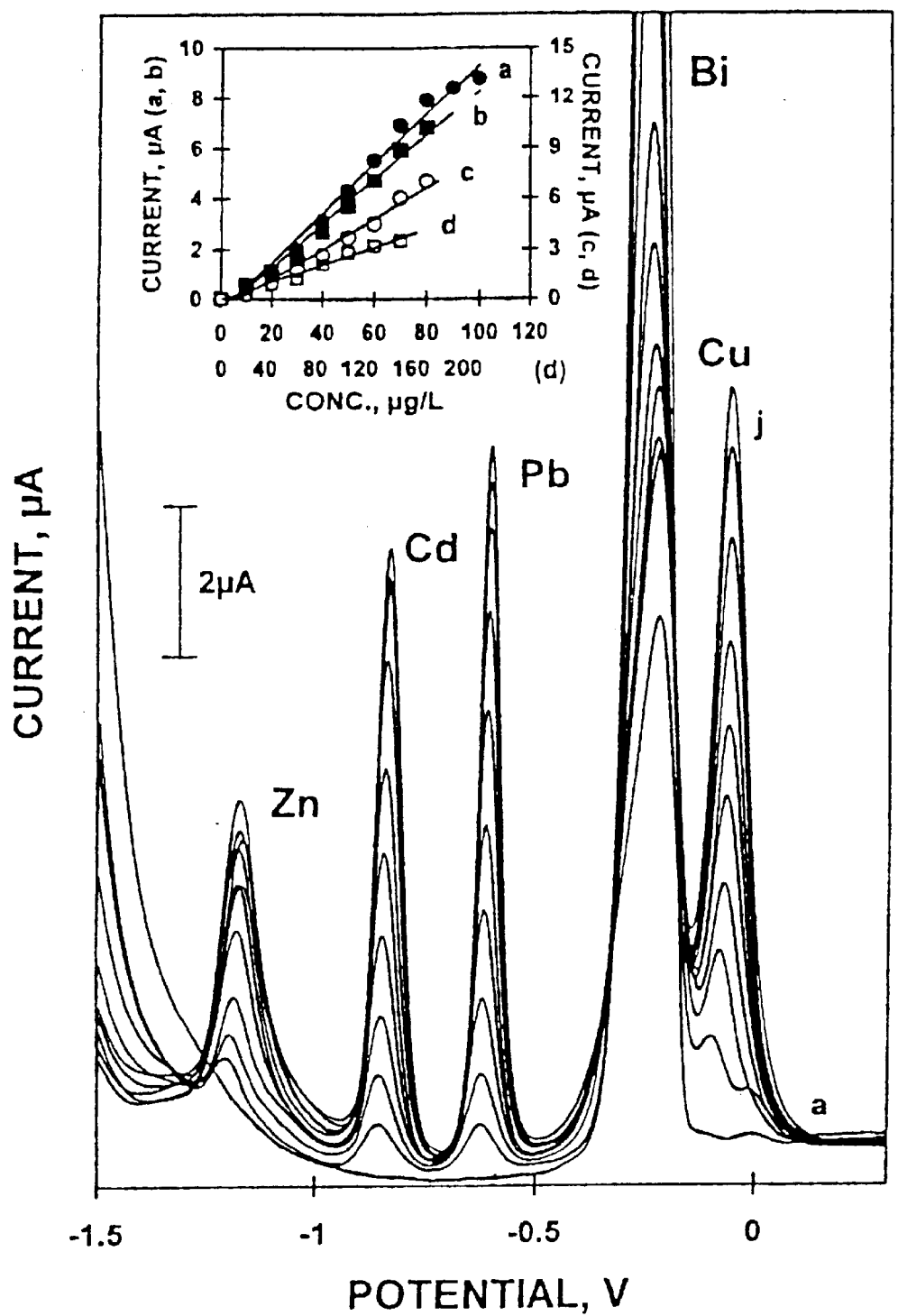
FIG. 12 are square-wave stripping voltammograms for detection of increasing concentration of copper, lead, cadmium in 10 $\mu$g/L steps and zinc in 20 $\mu$g/L steps, together with calibration plots.

Use of a bismuth-film electrode for simultaneously measuring copper, lead, cadmium, and zinc is illustrated in FIG. 12. FIG. 12 displays stripping voltammograms for increasing concentrations of the four metals in steps of 10 µg/L (Cu, Pb, Cd) or 20 µg/L (Zn). The four peaks are well resolved and increase linearly with the metal concentration, with only the copper signal slightly distorted. It appears that co-deposition of copper, using 10–80 µg/L solutions, has a small effect upon the quantitation of cadmium, lead, and zinc, despite the Cu—Zn intermetallic phenomenon and the Cu/Bi surface competition. The voltammogram in FIG. 12a clearly indicates that 10 to 20 µg/L concentrations can be measured readily and simultaneously following a short deposition time of 2 minutes. The gradual improvement in the hydrogen overvoltage background apparently reflects the continuous growth of the bismuth layer. The voltammograms of FIG. 12 resulted in relatively linear calibration plots (see inset) with slopes of 98 (Pb) (a), 87 (Cu) (b), 90 (Cd) (c) and 53 (Zn) (d) nA.L/µg, and correlation coefficients of 0.988, 0.987, 0.982, and 0.983, respectively.

EXAMPLE 18

A semi-automatic screen printer (Model TF 100; MPM, Franklin, Mass.) was used for printing carbon thick-film electrodes. The carbon ink (Acheson) was printed though a patterned stencil on 10 cm×10 cm ceramic plates containing 30 strips (3.3 cm×1.0 cm each). The resulting printed carbon thick-film electrodes were cured for 40 minutes at 50° C. A silver contact layer (utilizing an Ercon silver ink) was printed for electrical contact, partially covering the printed carbon film. An insulating ink (Ercon) was subsequently printed on a portion of the plate, resulting in 6 mm×2 mm sections on both ends for defining the working electrode and electrical contact. The insulating layer was cured at 50° C. for 3 hours. A bismuth film was preplated by immersing the screen-printed carbon electrode in a nondeaerated and stirred bismuth plating solution (100 mg/L Bi (III) in an acetate buffer (0.1 M, pH 4.5) and applying a potential of −0.8 V for 4 minutes. The bismuth-coated thick-film electrode was then rinsed carefully with deionized water and ready to use. The bismuth-coated screen-printed carbon electrode served as the working electrode, with an Ag/AgCl (3 M NaCl) and platinum wire acting as the reference and counter electrodes, respectively.

The bismuth-coated screen-printed carbon electrode, together with the Ag/AgCl reference and a platinum counter electrodes, were inserted into a 10 mL cell containing acetate buffer (0.01 M, pH 4.5) blank electrolyte solution. The deposition potential, usually −1.0 V, was applied to the screen-printed working electrode while the solution was stirred. Following the pre-concentration step, usually 120 seconds, the stirring was stopped, and after 10 seconds the voltammogram was recorded by applying a positive-going square-wave voltammetric potential scan with a frequency of 25 Hz, amplitude of 25 mV and potential step of 4 mV. The scan was terminated at −0.3 V. Following a test cycle, a 10-second conditioning step at −0.35 V was used to remove the target metal prior to the next cycle. A mercury-coated screen-printed electrode was employed for comparison, with measurement procedures similar to those employed with the bismuth-coated electrodes. All experiments were carried out at room temperature and in the presence of dissolved oxygen.

EXAMPLE 19

Figure 13:
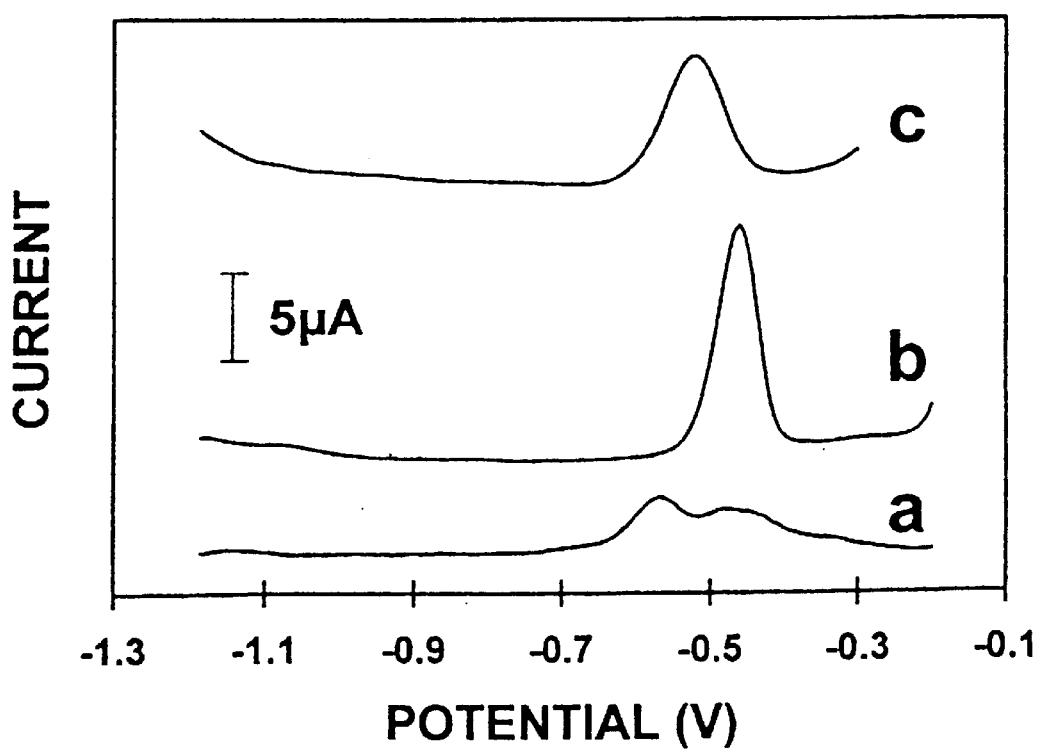
FIG. 13 are stripping voltammograms for trace lead at bare carbon (a), mercury-coated (b) and bismuth-coated (c) screen-printed electrodes.

FIG. 13 depicts stripping voltammograms utilizing the apparatus and method of Example 18 for trace lead at the bare carbon (a), mercury-coated (b) and bismuth-coated (c) screen-printed electrodes. The analyte solution was 0.01 M acetate buffer at pH 4.5 containing 50 $\mu$g/L lead (II). The bare carbon screen-printed electrode (a) displayed a poorly defined response, with both the mercury (b) and bismuth (c) coated electrodes resulting in defined lead signals that permit quantitation of trace lead. Both coated electrodes displayed a small background current over a wide potential range.

EXAMPLE 20

Figure 14:
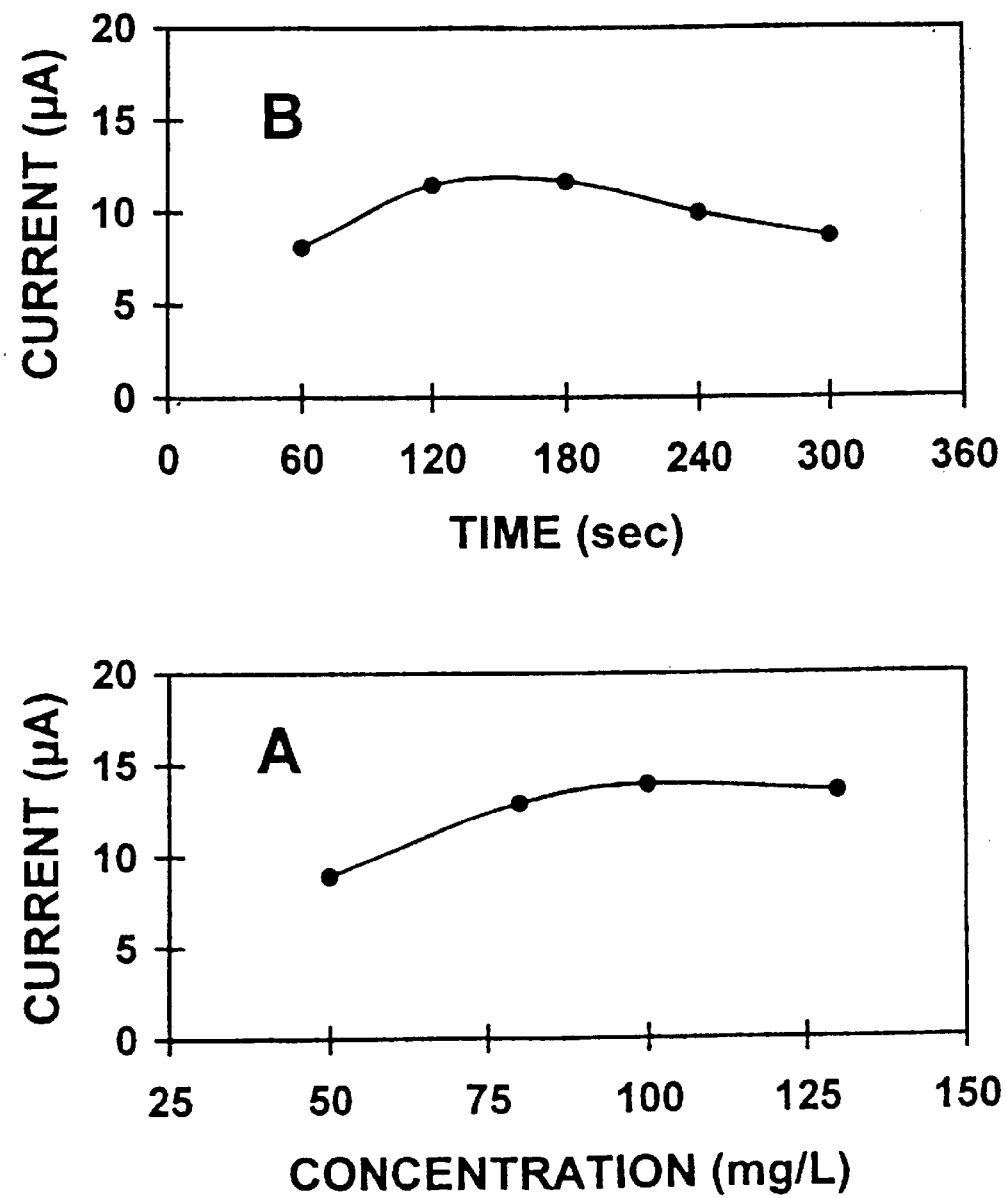
FIG. 14 are graphs of the effect of the bismuth concentration (A) and plating time (B) on the response to 60 $\mu$g/L lead(II)

FIG. 14 illustrates the effect of the bismuth concentration (A) and plating time (B) on the response to 60 $\mu$g/L lead (II), using the apparatus and method of Example 18. A 0.1 M acetate buffer was used for preparation and 0.01 M acetate buffer for analysis, both at pH 4.5, with deposition for 120 seconds at −1.2 V. The lead signal increased by about 25% on raising the bismuth concentration from 50 to 75 mg/L, and commenced leveling off above 100 mg/L (A). The response increased by about 30% on increasing the bismuth plating time from one to two minutes, and decreased slightly and gradually above three minutes (B). Subsequent work employed a bismuth concentration of 100 mg/L and 4 minutes plating at −0.8 V. Scanning electron micrographs of the resulting surfaces, using 5000× magnification, showed low coverage of bismuth, with non-uniform plating particularly within the voids between the 'flake-shaped' carbon particles.

EXAMPLE 21

Figure 15:
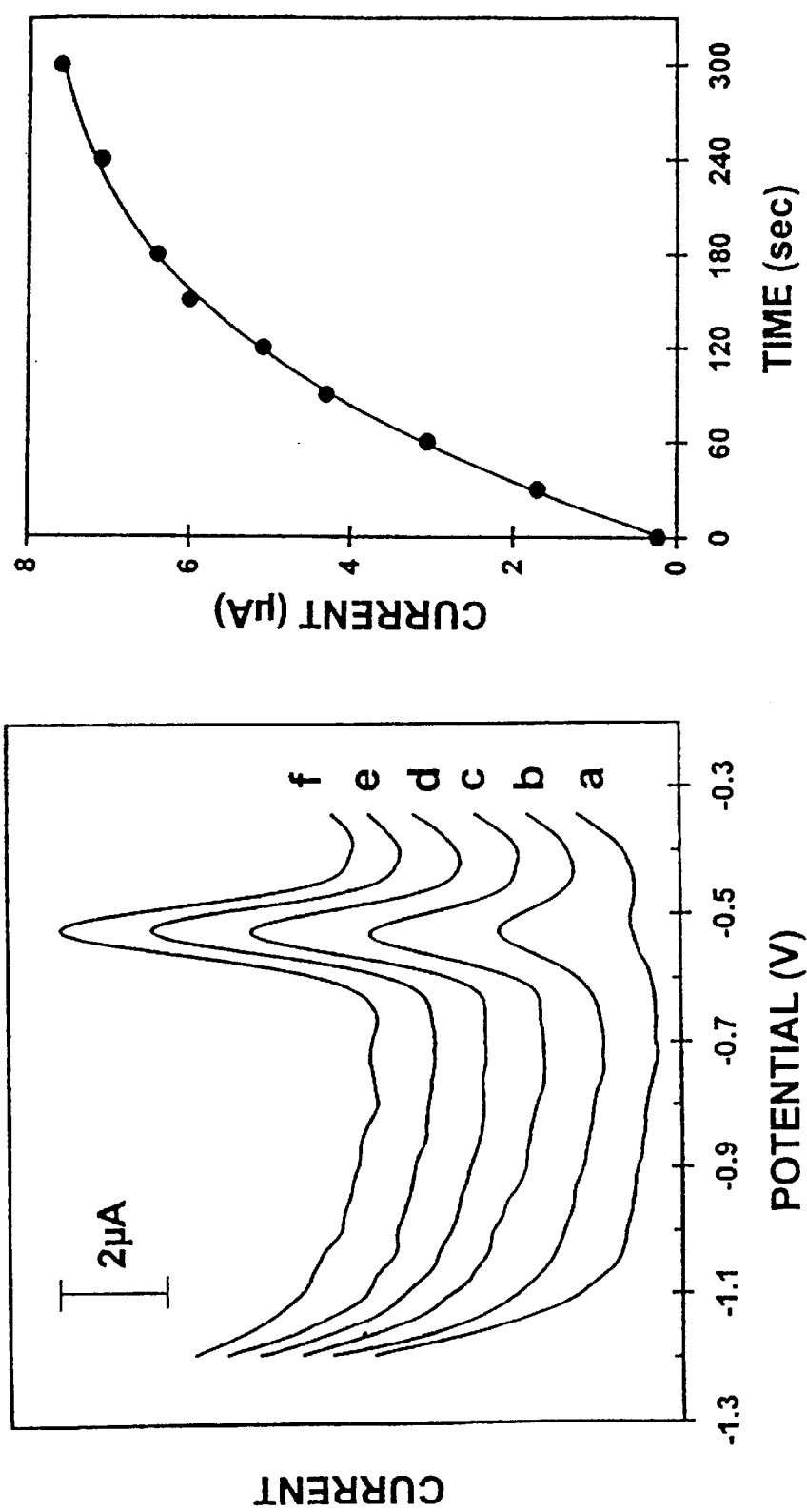
FIG. 15 are stripping voltammograms for a 60 $\mu$g/L lead (II) solution at pre-concentration times (in seconds) of 0 (a), 30 (b), 60 (c), 90 (d), 120 (e), and 150 (f), together with the resulting plot (as inset)

FIG. 15 depicts stripping voltammograms for a 60 $\mu$g/L lead (II) solution utilizing pre-concentration times of 0 (a), 30 (b), 60 (c), 90 (d), 120 (e), and 150 (f) seconds, utilizing the apparatus and methods of Example 18. FIG. 15 also depicts the resulting plot. Well-defined lead peaks increased rapidly upon increasing the pre-concentration time. While quantitation is not possible without deposition, very short accumulation times, on the order of 30 seconds or less, are sufficient to obtain favorable lead signals. The resulting plot of peak current versus deposition time in FIG. 15 is characterized by a rapid rise in the signal up 120 seconds deposition, and a slower change for longer periods. The influence of deposition potential was less profound, with only a negligible change in sensitivity observed on changing the deposition potential between −0.7 and −1.2 V, but with the response nearly doubling between −0.6 and −0.7 V.

EXAMPLE 22

Figure 16:
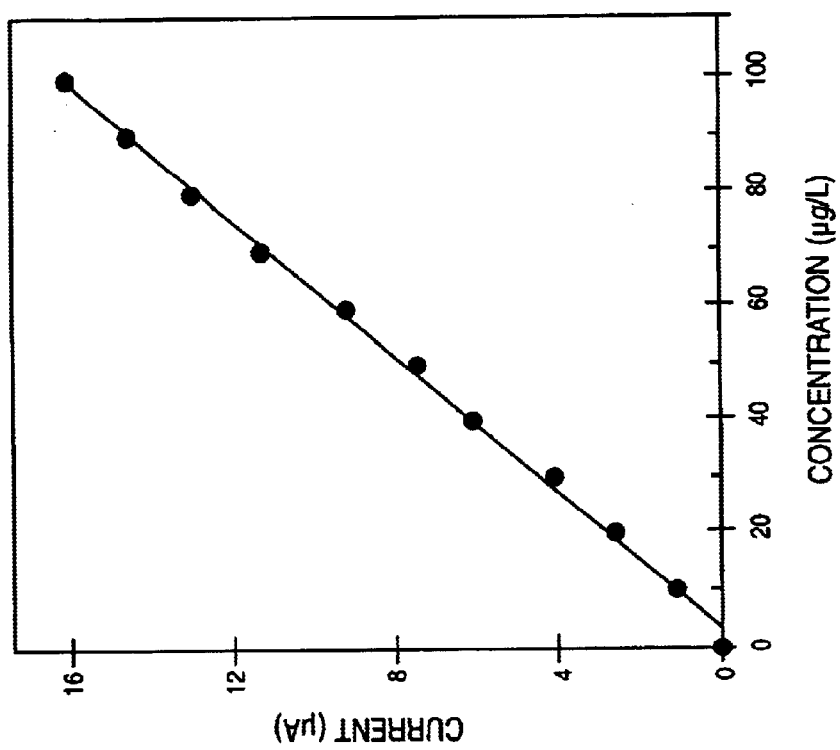
FIG. 16 are stripping voltammograms for detection of increasing levels of lead (II) in 10 $\mu$g/L steps (a–j), along with the background response (dotted line), and (on the right) the resulting calibration plot.
Figure 16:
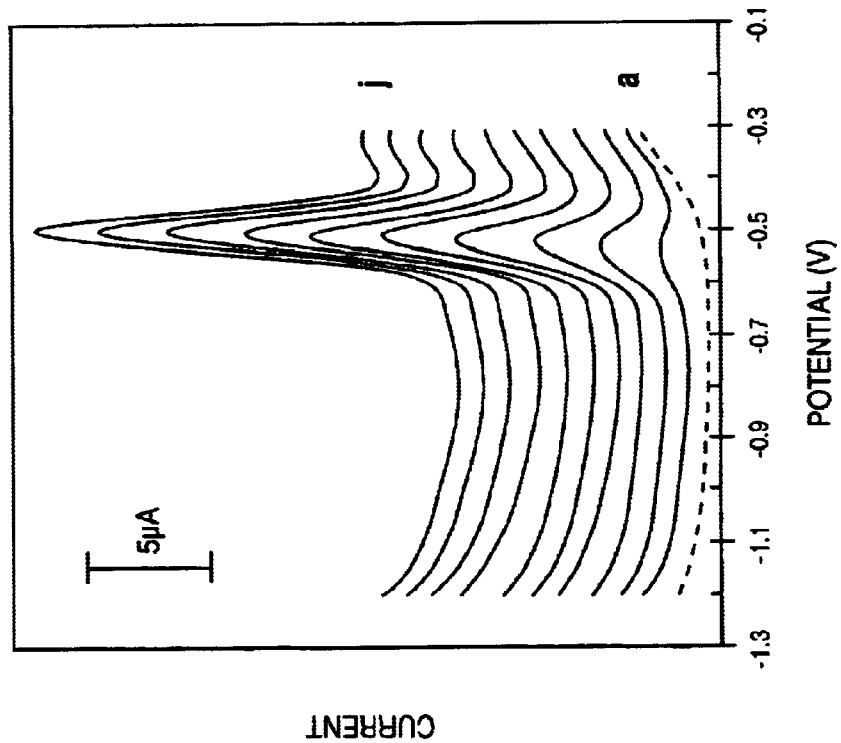

Stripping voltammograms for increasing levels of lead (II) in 10 $\mu$g/L steps (a–j), along with the background response (dotted line), are shown in FIG. 16, utilizing the apparatus and methods of Example 18. Also shown in FIG. 16 is the resulting calibration plot. Well-defined peaks were observed following a 2 minute deposition period, with the peak current increasing proportionally with the metal concentration to yield a highly linear calibration plot with a slope of 0.166 $\mu$A/ppb (correlation coefficient, 0.998). This response characteristic, coupled with the low background signal (dotted line), permits quantitation of low ppb levels of lead. Even lower concentrations can be detected utilizing longer deposition periods, with a detection limit of approximately 0.3 $\mu$g/L estimated on the basis of the signal-to-noise characteristics (S/N=3) of the response for a 1.0 $\mu$g/L lead solution following a 10 minute accumulation. The sensitive response of the bismuth electrode is also highly reproducible, as indicated from the relative standard deviation (7.4%) obtained for a series of 10 repetitive measurements of 20 $\mu$g/L lead.

EXAMPLE 23

The apparatus and methods of Example 18 were used to measure lead in drinking water samples. Utilizing a 2 minute deposition, defined lead sample peak resulted allowing quantitation following successive 4 ppb standard additions of lead. A lead sample value of 1.8 ppb was calculated from the resulting linear standard-addition plot (correlation coefficient, 0.999).

EXAMPLE 24

An EG&G PAR model 264A polarographic analyzer/stripping voltammeter was used in connection with Ag/AgCl reference and platinum counter electrodes, and a bismuth-film working electrode. An EG&G 303 mercury drop electrode and mercury-coated glassy carbon electrode (BAS) were used for comparison. A nickel standard stock solution was obtained from Aldrich and diluted as required. Solutions of 1000 mg/L bismuth and mercury, used for the deposition of the bismuth and mercury film electrodes, were prepared by diluting the corresponding standard stock solutions. Dimethylglyoxime (DMG) was received from Aldrich and a 0.01 M DMG solution was prepared in 50% ethanol. A 0.01 M ammonia buffer solution (pH 9.0) served as the supporting electrolyte. A well-polished glassy carbon electrode was immersed into a 0.1 M acetate buffer solution (pH 4.5) containing 1000 mg/L Bi(III). The deposition of the bismuth film proceeded for 8 minutes while holding the electrode at −1.0 V and stirring the solution. The bismuth-coated glassy carbon electrode was then washed carefully with double distilled water. For comparison, the mercury-coated glassy carbon electrode was prepared by using a 0.1 M HCl/1000 mg/L Hg(II) solution and depositing for 8 minutes at −0.6 V. A 10 mL electrolyte solution (0.01 M ammonia buffer pH 9.0), containing $10^{-5}$ M DMG, was used in the stripping operation. The accumulation potential (usually −0.7 V) was applied to the film electrode while the solution was stirred. Following the preconcentration step, the stirring was stopped and after a 15 second equilibrium time, the voltammogram was recorded by applying a negative-going linear potential scan at 50 mV $s^{-1}$. The scan was terminated at −1.4 V. Aliquots of the nickel standard solution were introduced after recording the background voltammogram.

EXAMPLE 25

Figure 17:
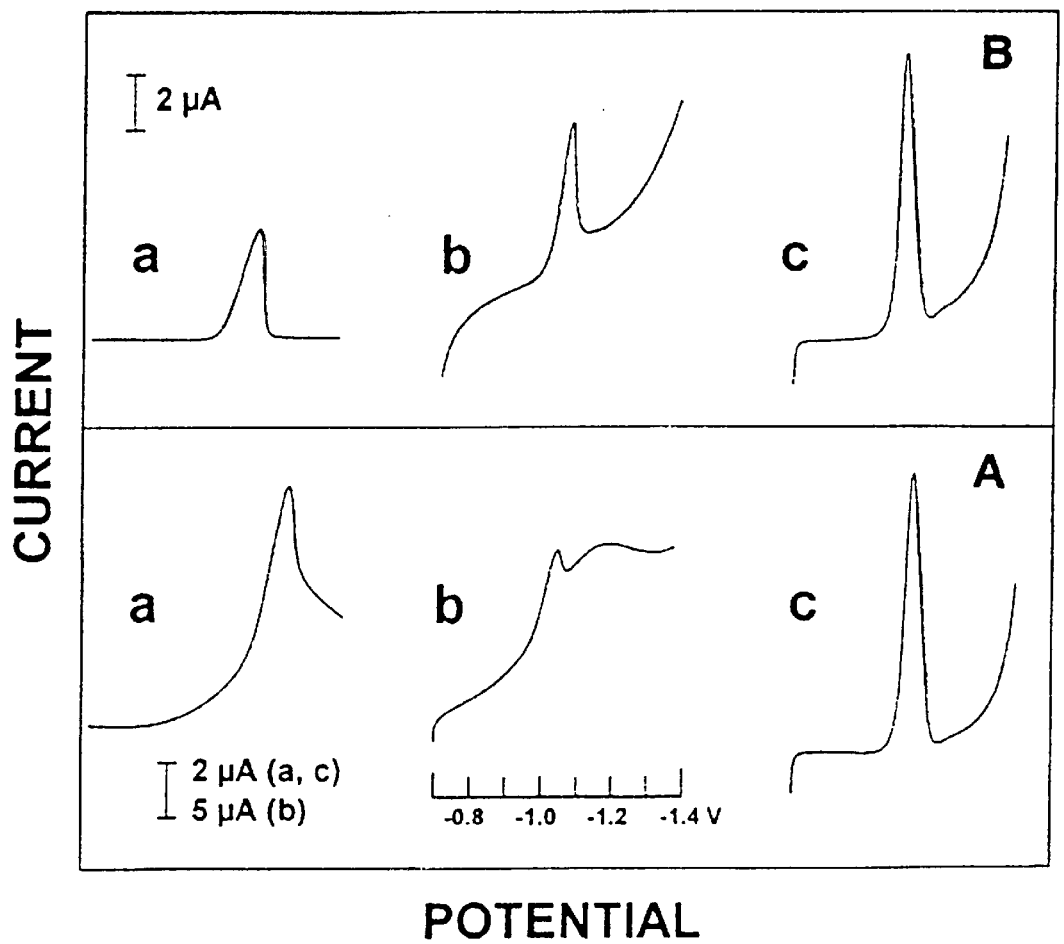
FIG. 17 are adsorptive stripping voltammograms of detection of 200 $\mu$g/L nickel in the presence (a) and absence (B) of oxygen at hanging mercury drop (a), mercury film (b) and bismuth film (c) electrodes.

FIG. 17 compares the adsorptive stripping voltammetric responses of the hanging mercury drop (a), mercury film (b), and bismuth film (c) electrodes to 200 μg/L (ppb) nickel following a 90 second accumulation from nondeaerated (A) and deaerated (B) solutions using the apparatus and methods of Example 24. The bismuth electrode displays a well-defined and sharp stripping peak (Ep=−1.03 V; $b_{1/2}$=46 mV), over a nearly flat background, in both solutions. The responses and the corresponding background current were nearly independent of the presence of oxygen. In contrast, using mercury electrodes the oxygen background contribution strongly overlapped with the nickel signal and did not permit convenient quantitation in the nondeaerated medium. Removing the oxygen eliminated the background interference at the hanging mercury drop electrode, but not at the mercury film electrode. Overall, the data of FIG. 17 indicate that the adsorptive stripping behavior of the bismuth-coated carbon electrode compares favorably with that of common mercury-based electrodes. In particular, the bismuth film offers a larger nickel-stripping peak, favorable signal-to-background characteristics, and is not prone to oxygen interference.

EXAMPLE 26

Figure 18:
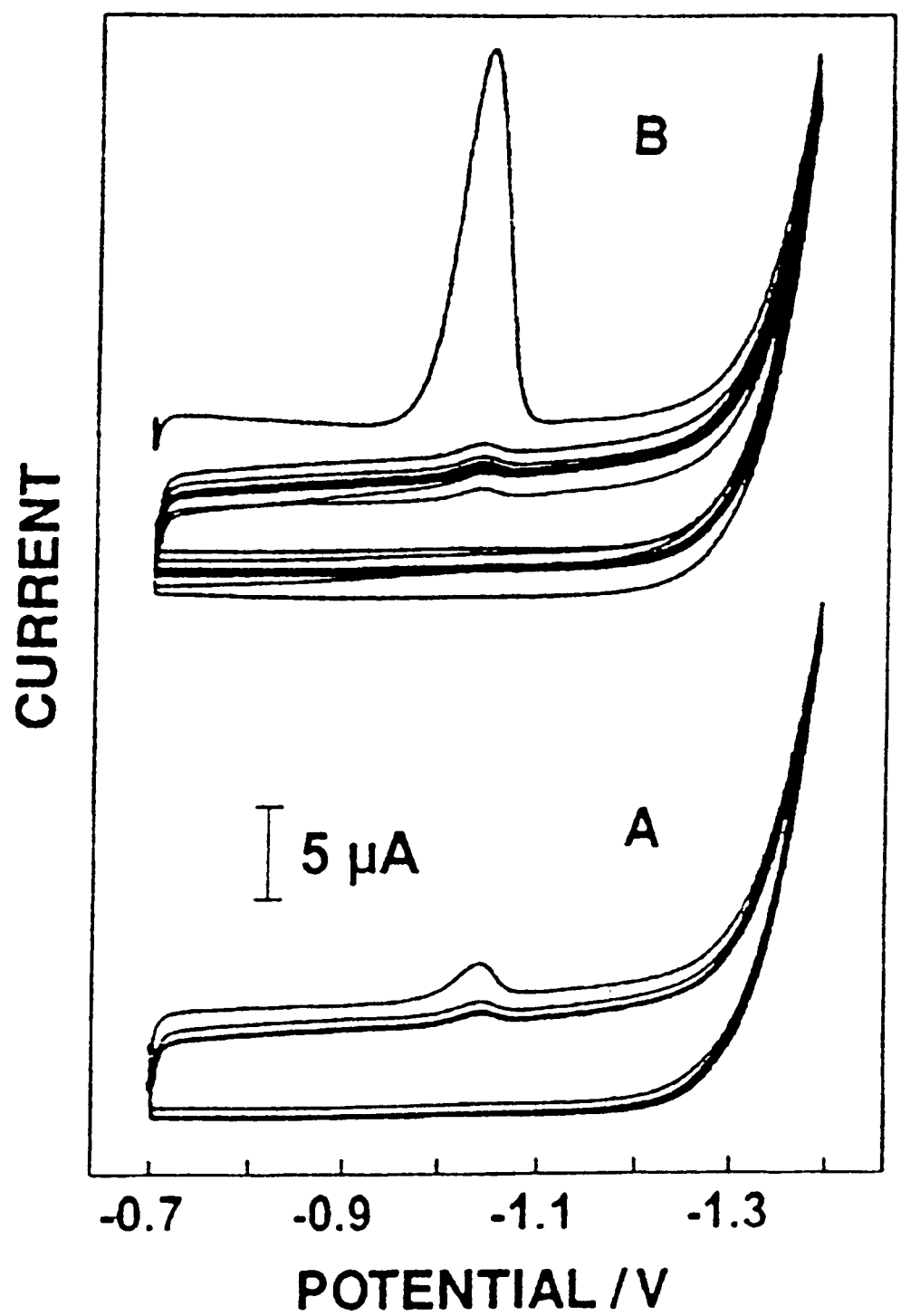
FIG. 18 are repetitive cyclic voltammograms for detection of 500 μg/L nickel.

FIG. 18 displays repetitive cyclic voltammograms for 500 μg/L nickel (in the presence of DMG) recorded without (A) and with (B) a preceding stirring period of 90 seconds using the apparatus and methods of Example 24. In both cases, a well-defined cathodic peak, due to the reduction of the chelate, is observed at the first scan; no oxidation peaks are observed upon scanning in the anodic direction. The reduction peak following the accumulation is 14-fold larger than that observed without a preceding stirring period. Subsequent scans exhibit substantially smaller and stable cathodic peaks, reflecting the desorption of the chelate.

EXAMPLE 27

Figure 19:
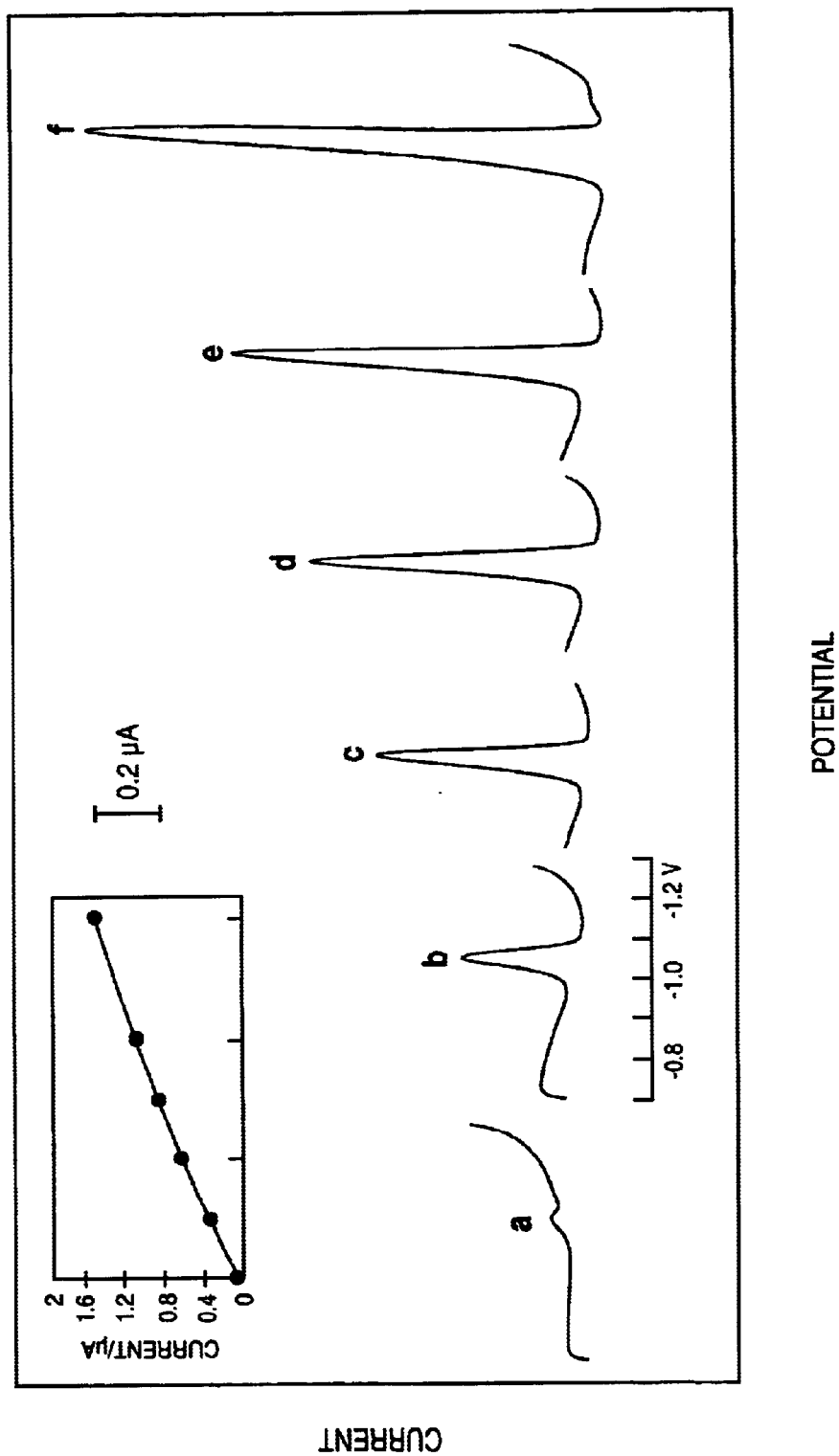
FIG. 19 are voltammograms of detection of 100 μg/L nickel at accumulation times of 0 (a), 30 (b), 60 (c), 90 (d), 120 (e) and 180 (f) seconds, with the inset the resulting plot of current vs. accumulation time.

The effect of the adsorption time was examined over the 0–180 second range as shown in FIG. 19, using the apparatus and methods of Example 24. The response of the bismuth electrode increased rapidly with the accumulation time. A 26-fold enhancement of the nickel peak was observed following an accumulation of 180 seconds. Nevertheless, 100 μg/L nickel could be detected in the nondeaerated sample even without prior accumulation (a). The resulting plot (shown on the inset of FIG. 19) is linear up to 60 seconds with a slight curvature thereafter. Changing the accumulation potential over the −0.4 to −0.9 V range had a negligible effect upon the adsorptive stripping response.

EXAMPLE 28

Figure 20:
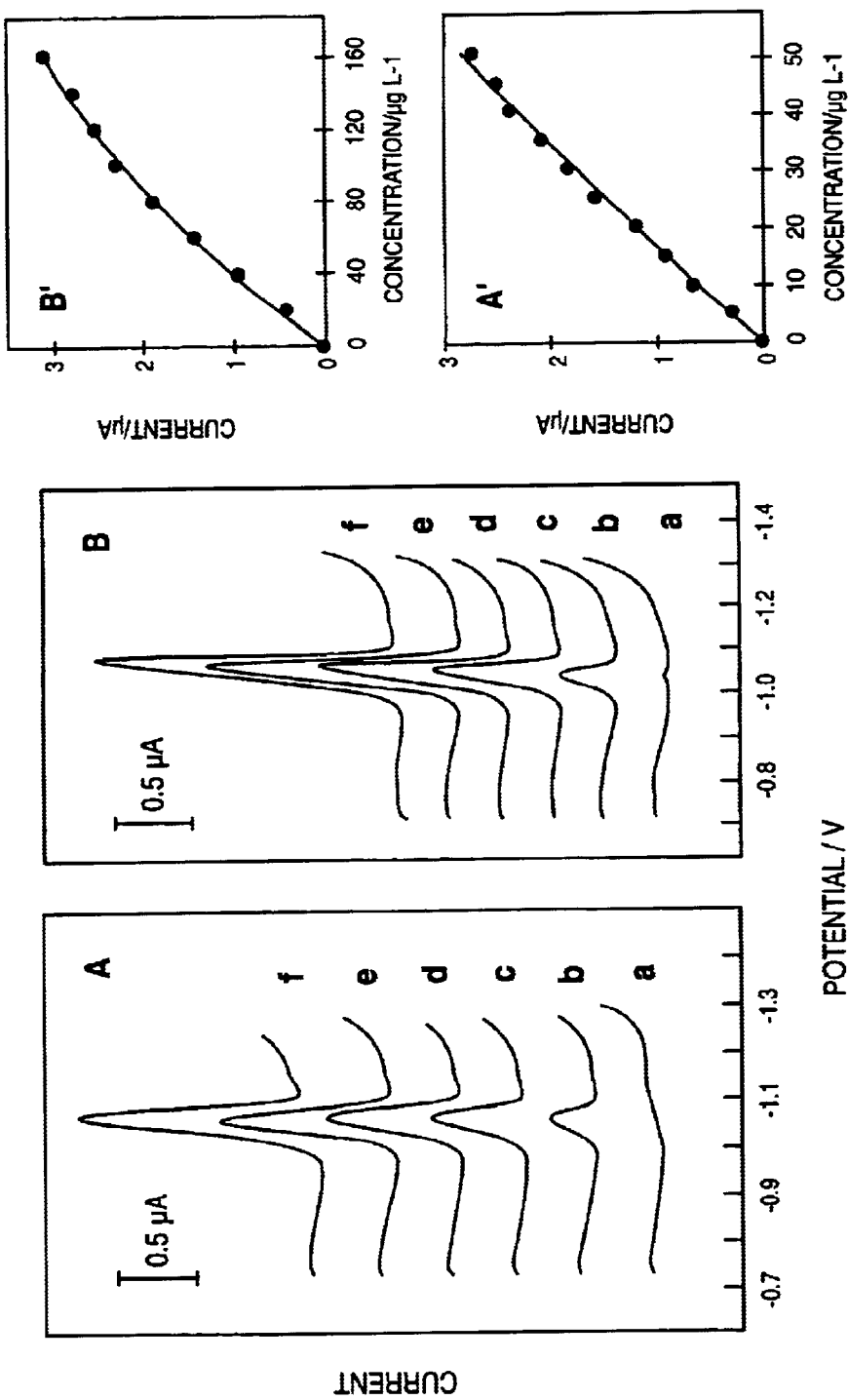
FIG. 20 are adsorptive stripping voltammograms obtained on increasing nickel concentration in 50 μg/L increments (A, b–f) and 200 μg/L increments (B, b–f), together with the resulting calibration plots.

FIG. 20 displays stripping voltammograms obtained upon increasing the nickel concentration in steps of 50 (A) and 200 (B) μg/L using the apparatus and methods of Example 24. Well-defined sharp peaks were observed over a flat baseline following 90 and 30 second deposition periods, respectively. While the 10 increments of 50 μg/L yielded a highly linear calibration plot (A'), the 200–1600 μg/L calibration study resulted in a slight curvature (above 800 μg/L) expected for adsorptive stripping experiments (B'). A detection limit of 8 μg/L nickel was estimated from the response for a 100 μg/L solution following a 3-minute adsorption (e.g., FIG. 20(*f*)). The high sensitivity was coupled to good reproducibility. A series of 14 repetitive measurements of 100 μg/L nickel yielded a very stable response with a relative standard deviation of 1.8%.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for analyzing metals in a solution sample comprising the steps of:
   disposing an electrode into the solution sample;
   adding a source of bismuth to the solution sample;
   applying a current to the electrode to deposit a bismuth metal film thereon; and then
   analyzing the solution sample for metal content using electrochemical stripping analysis with the electrode.

2. The method of claim 1, wherein the electrode comprises carbon.

3. The method of claim 2, wherein the electrode is an electrode selected from the group consisting of glassy-carbon disk electrodes, carbon-fiber microelectrodes, thin-film electrodes and thick-film electrodes.

4. The method of claim 2, wherein the electrode is a screen-printed electrode.

5. The method of claim 1, further comprising the step of providing at least one reference electrode.

6. The method of claim 1, wherein the step of analyzing the solution sample for metal content using electrochemical stripping analysis comprises a method of analysis selected from the group consisting of stripping voltammetry and stripping potentiometry.

7. The method of claim 6, wherein the stripping voltammetry comprises anodic stripping voltammetry.

8. The method of claim 6, wherein the stripping voltammetry comprises adsorptive stripping voltammetry.

9. The method of claim 1, wherein the step of analyzing the solution sample for metal content further comprises use of bismuth as an internal standard.

10. The method of claim 1, wherein the step of analyzing the solution sample for metal content further comprises quantitative determination.

11. The method of claim 1, wherein the step of analyzing the solution sample for metal content further comprises analyzing the solution sample for more than one metal.

12. The method of claim 1, wherein the solution sample is a sample of body fluid.

13. The method of claim 1, wherein the concentration of bismuth in the solution sample is between about 500 µg/L and about 1000 mg/L.

14. A method for analyzing metals in a solution sample comprising the steps of:
   disposing an electrode in a first solution comprising bismuth;
   electrolytically depositing a bismuth metal film on the electrode;
   removing the electrode from the first solution and disposing it into the sample solution; and
   applying a current to the electrode and analyzing the solution sample for metal content using electrochemical stripping analysis.

15. The method of claim 14, wherein the electrode comprises carbon.

16. The method of claim 15, wherein the electrode is an electrode selected from the group consisting of glassy-carbon disk electrodes, carbon-fiber microelectrodes, thin-film electrodes and thick-film electrodes.

17. The method of claim 15, wherein the electrode is a screen-printed electrode.

18. The method of claim 14, further comprising the step of providing at least one reference electrode.

19. The method of claim 14, wherein the step of analyzing the solution sample for metal content using electrochemical stripping analysis comprises a method of analysis selected from the group consisting of stripping voltammetry and stripping potentiometry.

20. The method of claim 19, wherein the stripping voltammetry comprises anodic stripping voltammetry.

21. The method of claim 19, wherein the stripping voltammetry comprises adsorptive stripping voltammetry.

22. The method of claim 14, wherein the step of analyzing the solution sample for metal content further comprises quantitative determination.

23. The method of claim 14, wherein the step of analyzing the solution sample for metal content further comprises analyzing the solution sample for more than one metal.

24. The method of claim 14, wherein the solution sample is a sample of body fluid.

* * * * *